(12) United States Patent
Lee

(10) Patent No.: US 8,246,684 B2
(45) Date of Patent: Aug. 21, 2012

(54) INTERVERTEBRAL DISC AND FACET JOINT PROSTHESIS

(75) Inventor: Casey K. Lee, Florham Park, NJ (US)

(73) Assignee: RE-Spine LLC., Florham Park, NJ (US)

( * ) Notice: Subject to any disclaimer, the term of this patent is extended or adjusted under 35 U.S.C. 154(b) by 1299 days.

(21) Appl. No.: 11/738,439

(22) Filed: Apr. 20, 2007

(65) Prior Publication Data
US 2008/0077245 A1    Mar. 27, 2008

Related U.S. Application Data

(60) Provisional application No. 60/793,256, filed on Apr. 20, 2006.

(51) Int. Cl.
*A61F 2/44* (2006.01)

(52) U.S. Cl. .................................. 623/17.15

(58) Field of Classification Search .... 623/17.11–17.16; 606/247
See application file for complete search history.

(56) References Cited

U.S. PATENT DOCUMENTS

| | | | |
|---|---|---|---|
| 5,507,816 A * | 4/1996 | Bullivant | 623/17.15 |
| 5,571,191 A | 11/1996 | Fitz | |
| RE36,758 E | 6/2000 | Fitz | |
| 6,132,430 A * | 10/2000 | Wagner | 606/264 |
| 6,132,464 A | 10/2000 | Martin | |
| 6,419,703 B1 | 7/2002 | Fallin et al. | |
| 6,610,091 B1 | 8/2003 | Reiley | |
| 6,830,570 B1 | 12/2004 | Frey et al. | |
| 6,840,944 B2 | 1/2005 | Suddaby | |
| 6,852,127 B2 | 2/2005 | Varga et al. | |
| 6,902,580 B2 | 6/2005 | Fallin et al. | |
| 6,949,123 B2 | 9/2005 | Reiley | |
| 7,556,651 B2 * | 7/2009 | Humphreys et al. | 623/17.15 |
| 7,635,389 B2 * | 12/2009 | Yu et al. | 623/17.15 |
| 7,682,395 B2 * | 3/2010 | Casey | 623/17.13 |
| 7,785,351 B2 * | 8/2010 | Gordon et al. | 606/259 |
| 7,799,082 B2 * | 9/2010 | Gordon et al. | 623/17.16 |

(Continued)

FOREIGN PATENT DOCUMENTS

WO    WO 2005/070353 A1    8/2005

(Continued)

OTHER PUBLICATIONS

Yang, K.H., et al., "Mechanism of Facet Load Transmission as a Hypothesis for Low-Back Pain", *SPINE*, vol. 9, No. 6, pp. 557-565, 1984.

(Continued)

*Primary Examiner* — Eduardo C Robert
*Assistant Examiner* — Jerry Cumberledge
(74) *Attorney, Agent, or Firm* — Miles & Stockbridge P.C.

(57) ABSTRACT

An intervertebral disc and facet joints prosthesis includes (i) an intervertebral disc prosthesis element having an upper rigid prosthesis endplate, a lower rigid prosthesis endplate, and a core interposed between and attached to the rigid endplates, and (ii) at least one facet joint prosthesis element, each facet joint prosthesis element including an upper facet joint prosthesis component and a lower facet joint prosthesis component. The upper facet joint prosthesis component is constructed to cooperate with its respective lower facet joint prosthesis component, the upper facet joint prosthesis component being rigidly fixed to the upper endplate and the lower facet joint prosthesis component being rigidly fixed to the lower endplate. The prosthesis may be implanted by surgical procedures involving a posterior or postero-lateral approach.

42 Claims, 23 Drawing Sheets

U.S. PATENT DOCUMENTS

| | | |
|---|---|---|
| 2003/0004572 A1 | 1/2003 | Goble et al. |
| 2004/0133281 A1* | 7/2004 | Khandkar et al. ......... 623/17.16 |
| 2004/0162563 A1 | 8/2004 | Michelson |
| 2004/0181284 A1 | 9/2004 | Simonson |
| 2004/0181285 A1 | 9/2004 | Simonson |
| 2004/0186574 A1 | 9/2004 | Varga et al. |
| 2004/0225365 A1 | 11/2004 | Eisermann et al. |
| 2005/0033431 A1 | 2/2005 | Gordon et al. |
| 2005/0033432 A1 | 2/2005 | Gordon et al. |
| 2005/0043797 A1 | 2/2005 | Lee |
| 2005/0043800 A1 | 2/2005 | Paul et al. |
| 2005/0049623 A1 | 3/2005 | Moore et al. |
| 2005/0055096 A1 | 3/2005 | Serhan et al. |
| 2005/0075644 A1 | 4/2005 | DiPoto et al. |
| 2005/0131409 A1 | 6/2005 | Chervitz et al. |
| 2005/0131545 A1* | 6/2005 | Chervitz et al. ........... 623/17.14 |
| 2005/0256578 A1* | 11/2005 | Blatt et al. ................. 623/17.15 |
| 2005/0273111 A1 | 12/2005 | Ferree et al. |
| 2005/0277930 A1* | 12/2005 | Parsons ........................... 606/61 |
| 2007/0112427 A1* | 5/2007 | Christy et al. ............. 623/17.11 |
| 2007/0270959 A1* | 11/2007 | Dubousset ................. 623/17.11 |

FOREIGN PATENT DOCUMENTS

WO    WO 2005/117725 A2    12/2005

OTHER PUBLICATIONS

El-Bohy, A.A., et al., "Experimental Verification of Facet Load Transmission by Direct Measurement of Facet Lamina Contact Pressure" *J Biomechanics*, vol. 22, No. 8/9, pp. 931-941, 1989.

Farfan, H.F., et al., "The Effects of Torsion on the Lumbar Intervertebral Joints: The Role of Torsion in the Production of Disc Degeneration", *The Journal of Bone and Joint Surgery*, vol. 52, No. 3, Apr. 1970, pp. 468-497.

Extended European search report, including search opinion, for European Patent Application No. 07761074.9, May 29, 2012.

\* cited by examiner

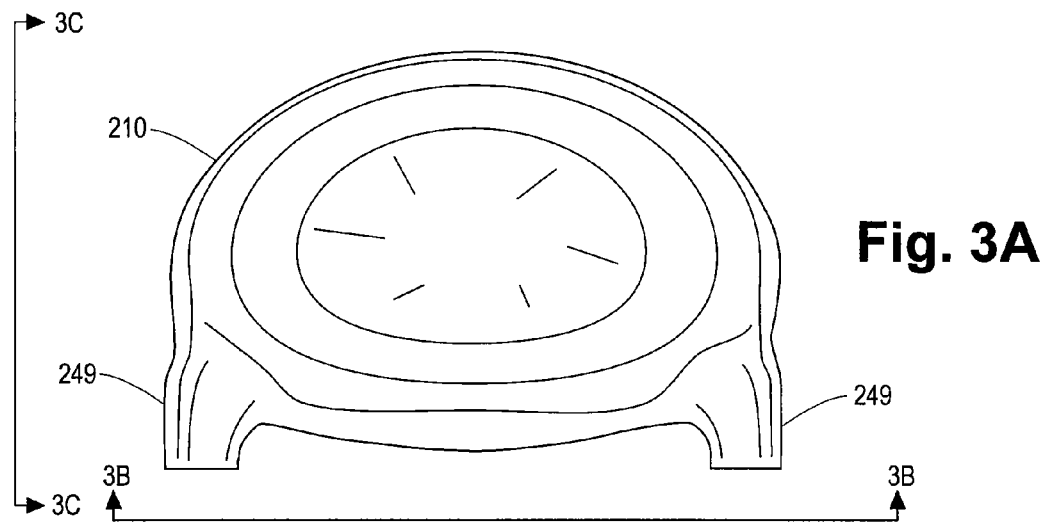
Fig. 3A
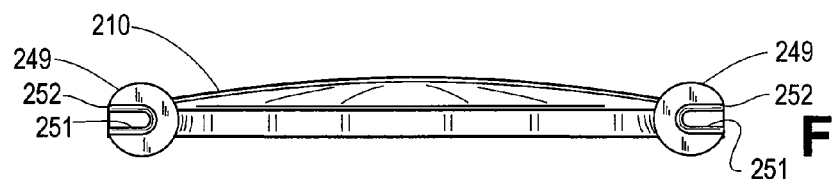
Fig. 3B
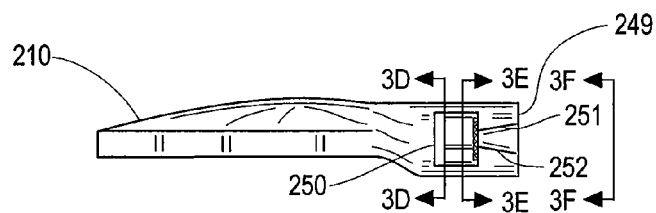
Fig. 3C
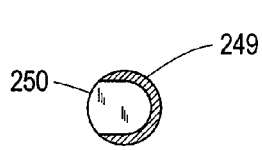 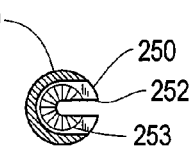 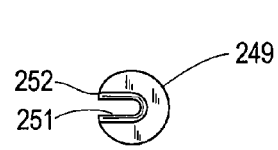
Fig. 3D   Fig. 3E   Fig. 3F

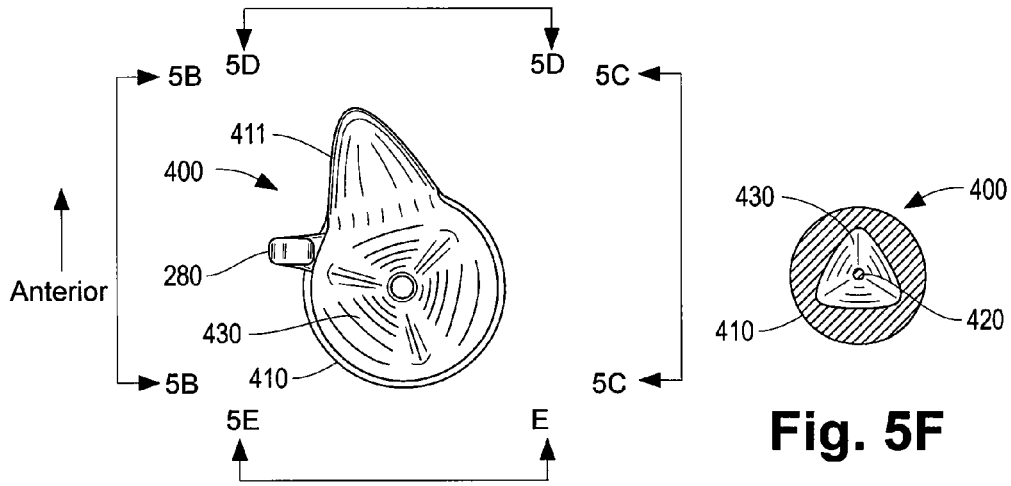
Fig. 5A
Fig. 5F
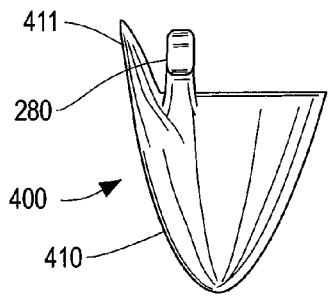
Fig. 5B
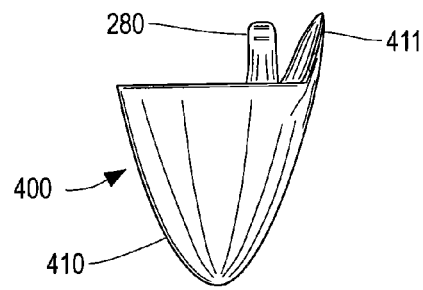
Fig. 5C
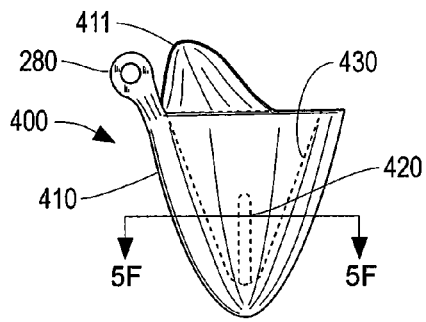
Fig. 5D
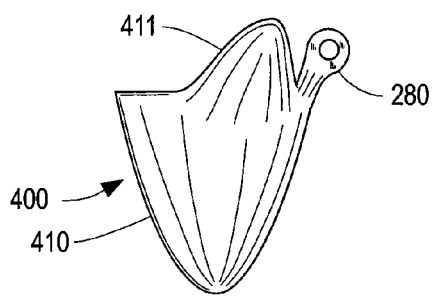
Fig. 5E

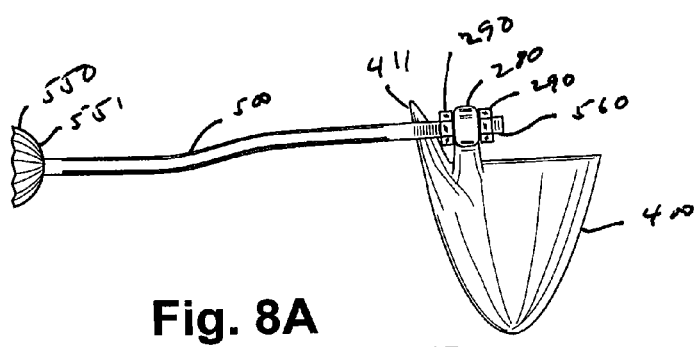
Fig. 8A
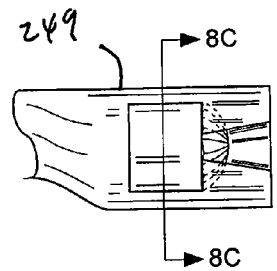 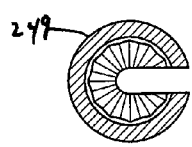 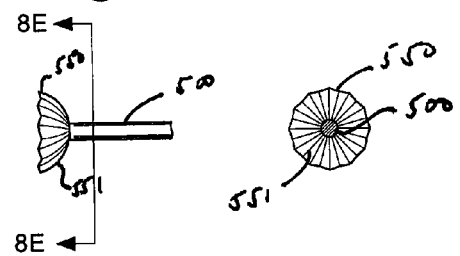
Fig. 8B　　Fig. 8C　　Fig. 8D　　Fig. 8E
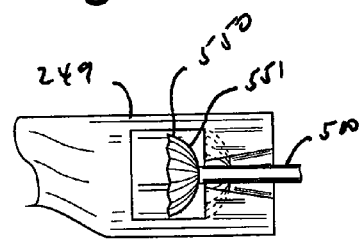 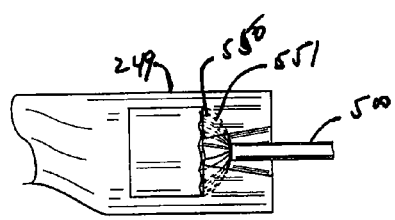
Fig. 8F　　　　　　Fig. 8G
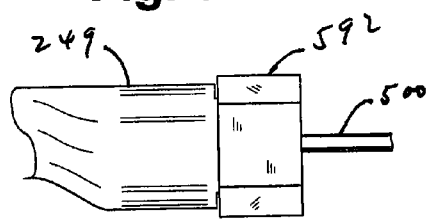 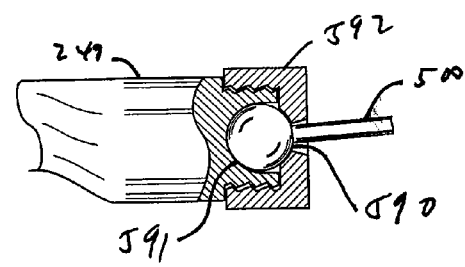
Fig. 8H　　　　　　Fig. 8J

INTERVERTEBRAL DISC AND FACET JOINT PROSTHESIS

CROSS-REFERENCE TO RELATED APPLICATION

This application claims the benefit of U.S. Provisional Patent Application No. 60/793,256, filed Apr. 20, 2006, the entire disclosure of which is incorporated herein by reference.

BACKGROUND OF THE INVENTION

1. Field of the Invention

This invention relates to prostheses for use in treating back pain and more particularly to prostheses for replacing an intervertebral disc and associated intervertebral facet joints.

2. Background

Lower back pain is a very common disorder and is responsible for extensive morbidity and lost time at work. The prevalence rate of low back pain is very high, affecting approximately 80% of the general population at some time. Although most patients experience the painful symptoms only occasionally and recover fully, approximately 10% of these patients experience chronic and disabling low back pain in spite of various medical treatments.

The most common cause of chronic disabling low back pain is degenerative disk disease (DDD). Another problem associated with low back pain, which often accompanies DDD, is degeneration of the facet joints between vertebrae.

The functional unit of the spinal column is a spinal motion segment that is made of a three-joint complex, a disc anteriorly and two facet joints posteriorly. The facet joint is a synovial joint with the joint surfaces covered by hyaline cartilage like other diarthrodial joints. The orientation of the facet joints in the lumbosacral spine is symmetrical on both sides in almost all individuals, but it is occasionally found to be asymmetrical. Facet asymmetry has been reported in the literature to cause disc degeneration. The facet joint is generally oriented obliquely in sagittal and coronal planes. The orientation of the facet joints is significantly different at different levels within the spine, i.e., the cervical, thoracic, thoraco-lumbar, and lumbo-sacral regions of the spine. Within the lumbar or lumbo-sacral spine the size, shape, orientation, and angle of the facet joints have a wide range of variation among the motion segments at different levels within an individual. Such variations are even greater among different individuals.

The pathology of degenerative disease of the spinal motion segment commonly begins with intervertebral disc degeneration. Such degeneration of the intervertebral disc frequently results in abnormal biomechanics of the spinal motion segment, which leads, in turn, to degeneration of the facet joints. Symptomatic degeneration of the intervertebral disc and/or the facet joints of a spinal motion segment have been treated by surgical replacement of the nucleus pulpous of the intervertebral disc, the entire intervertebral disc, and/or the facet joints, with appropriate prostheses.

Replacement of the intervertebral disc with an artificial disc prosthesis is indicated for patients having isolated disc degeneration without accompanying degeneration of the facet joints. However, the presence of significant arthritis of the facet joints is a contraindication for implantation of a disc prosthesis alone. Nevertheless, most patients presenting with severe arthritis of the facet joints have concomitant severe disc degeneration. Surgical treatment of these patients requires either spinal fusion or replacement of both the intervertebral disc and the facet joints. Hitherto, most intervertebral disc prostheses have been designed to be implanted by an anterior replacement procedure through the retroperitoneal approach, while replacement of the facet joints evidently requires a posterior approach.

In order to simplify the surgical procedures required for treating patients by replacement of both the intervertebral disc and the facet joints, various posterior approaches have been proposed. For example, it has been proposed to expose the intervertebral disc through a posterior approach by resecting one or both pairs of facet joints, surgically removing the degenerated disc and replacing it with a suitable prosthesis, and then replacing the facet joints with a suitable prosthesis. In other procedures, the facet joints are spared, which limits the surgical access area for approach to the intervertebral disc typically to a region having a diameter of not more than 1.5 cm. Such limitation, in turn, requires that the size of the prosthesis be relatively small, and has resulted in the use of disc prostheses that are expandable after insertion, or the implantation of two or more small prostheses. The use of such small prostheses may affect the stability of the prosthesis within the intervertebral space, because it is generally considered that the surface area of the contact between the disc prosthesis and the vertebral endplate has to be no less than about 6.5 square centimeters in order to prevent subsidence of the prosthesis.

Hitherto, facet joint prostheses have been anchored to the vertebral bone through one or more of the posterior vertebral structures, i.e., the pedicles, the transverse processes, the spinous process, the laminae, or the inferior articular process. However, such fixation methods must be evaluated by their ability to solve the serious problem of secure fixation of the prosthetic components to the bone. During the physiologic range of motion, the facet joint is under severe shear, bending, and torsional loads. Accordingly, secure fixation of facet joints prostheses to the bone during fatigue loads is a serious challenge.

Accordingly, a need has continued to exist for a prosthesis, implantable through a posterior approach, that could replace both the intervertebral disc and one or both of the facet joints, thus avoiding problems, such as vascular complications, associated with intervertebral disc replacement through the anterior approach.

SUMMARY OF THE INVENTION

The problems associated with known prostheses and methods for replacing an intervertebral disc and facet joints are alleviated by the prosthesis of the invention, which includes:

an intervertebral disc prosthesis element including an upper rigid prosthesis endplate, a lower rigid prosthesis endplate, and a core interposed between and attached to the rigid endplates, and at least one facet joint prosthesis element, each facet joint prosthesis element including an upper facet joint prosthesis component and a lower facet joint prosthesis component, the upper facet joint prosthesis component being constructed to cooperate with its respective lower facet joint prosthesis component, and the upper facet joint prosthesis component being rigidly fixed to the upper endplate and the lower facet joint prosthesis component being rigidly fixed to the lower endplate.

Accordingly, it is a feature of the invention to provide prostheses for treatment of intervertebral disc disease that can be implanted through a posterior or postero-lateral surgical approach.

A further feature is to provide prostheses which allow implantation of both an intervertebral disc prosthesis and a facet joint prosthesis through a posterior or postero-lateral approach.

A further feature of the invention is to provide a surgical procedure for implantation of intervertebral disc prostheses and/or facet joint prostheses through a posterior and/or postero-lateral approach.

A further feature is to provide a surgical procedure for implantation of intervertebral disc prostheses and/or facet joint prostheses that can minimize or avoid vascular and other complications associated with anterior procedures for intervertebral disc replacement.

Further features of the invention will be apparent from the description of the invention which follows.

BRIEF DESCRIPTION OF THE DRAWINGS

FIG. 3A is a plan view of an upper endplate of the intervertebral disc element showing a vertebra-contacting surface wherein the surface has a generally dome-shaped configuration.

FIG. 3B shows a posterior elevational view of the endplate of FIG. 3A in the direction indicated by the arrows 3B-3B in FIG. 3A.

FIG. 3C shows a side elevational view of the prosthesis endplate of FIG. 3A in the direction indicated by the arrows 3C-3C in FIG. 3A.

FIG. 3D shows a detail of the attachment extension for the mechanical coupling apparatus (connecting rod) as shown particularly by the cross section 3D-3D indicated in FIG. 3C.

FIG. 3E shows a detail of the attachment extension for the mechanical coupling apparatus (connecting rod) as shown particularly by the cross section 3E-3E indicated in FIG. 3C.

FIG. 3F shows a detail of the attachment extension for the mechanical coupling apparatus (connecting rod) in the direction shown by the arrowed line 3F-3F in FIG. 3C.

FIG. 5A is plan view of a cone component of the facet joint prosthesis element of the invention.

FIG. 5B is a lateral elevational view of the cone component of FIG. 5A.

FIG. 5C is a medial elevational view of the cone component of FIG. 5A.

FIG. 5D is a posterior elevational view of the cone component of FIG. 5A.

FIG. 5E is an anterior elevational view of the cone component of FIG. 5A.

FIG. 5F is a cross sectional view of the cone component of FIGS. 5A-5E, taken along the line 5F 5F in FIG. 5D.

FIG. 8A shows an assembly of the cone element of the prosthesis of the invention and its connecting rod for connecting to a connecting or attachment extension of an upper disc prosthesis element endplate, wherein the connecting rod has a serrated head.

FIG. 8B shows a lateral elevational detail of an upper endplate connecting extension having a serrated recess for receiving a serrated head of a connecting rod.

FIG. 8C shows a cross-section of the connecting extension of FIG. 8B taken at the line 8C-8C in FIG. 8B.

FIG. 8D shows a lateral elevational view of the attachment end of a connecting rod having a serrated head FIG. 8E shows an elevational view of the rod head of FIG. 8D, taken at the line 8E-8E in FIG. 8D.

FIG. 8F illustrates a first step in the connection of a connecting rod, such as that of FIG. 8D, with an endplate attachment extension, such as that of FIG. 8B.

FIG. 8G illustrates the final position in the connection of a connecting rod, such as that of FIG. 8D, with an endplate attachment extension, such a that of FIG. 8B, wherein the serrated head of the connecting rod is seated in the serrated recess of the endplate attachment extension.

FIG. 8H is a lateral elevational view of an alternate connection between a connecting rod and a connecting endplate extension incorporating a ball joint.

FIG. 8J is a partial cross-section of the connecting extension and ball joint showing the ball and socket joint.

DETAILED DESCRIPTION OF THE INVENTION

Figure 1:
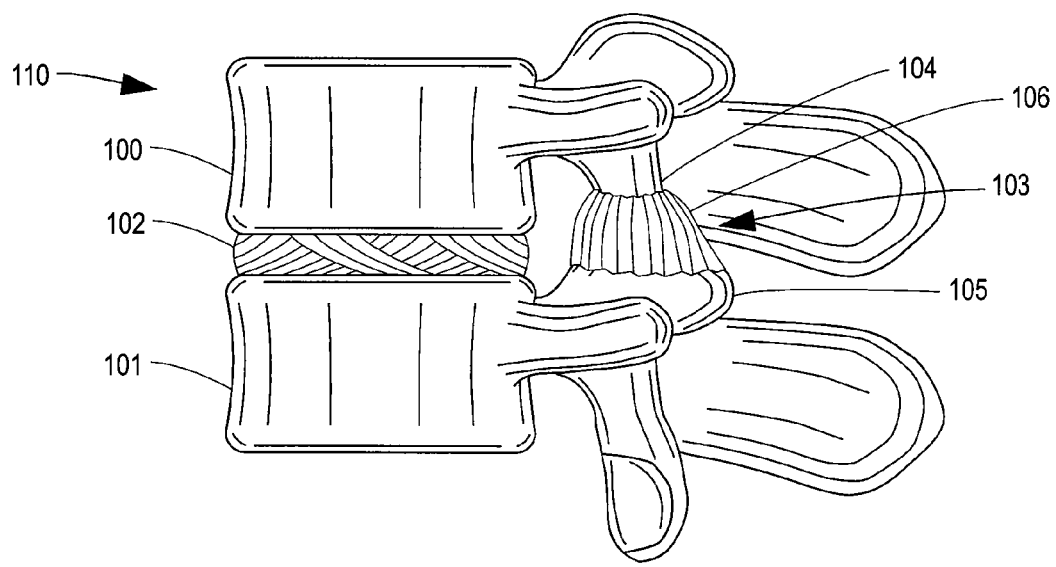
FIG. 1 shows a lateral elevational view of a human spinal motion segment.

The intervertebral disc and facet joint prosthesis of the invention includes
1) an intervertebral disc prosthesis element;
2) at least one facet joint prosthesis element; and 3) structure rigidly connecting the intervertebral disc element and at least one component of the facet joint prosthesis element.

1.) The Intervertebral Disc Prosthesis Element:

The disc prosthesis element includes upper and lower substantially rigid endplates, and a core interposed between and attached to the rigid endplates.

The rigid endplates are typically provided with domed surfaces facing the adjacent vertebrae for contacting the vertebral endplates. These surfaces may include bosses shaped and sized to mate with complementary recesses formed in the vertebral endplates. For example, the domed surface of the rigid endplates may have a heart-shaped configuration matching a correspondingly shaped recess made in the vertebral endplate, e.g., by an appropriately shaped milling cutter or reamer, using a bilateral approach as described below. Alternatively, if the recess in the vertebral endplate is made using a unilateral approach, the recess may be a generally cylindrical groove or an elliptically shaped recess with the long axis thereof oriented obliquely from the posterior-lateral region (10-11 o'clock or 1-2 o'clock point, wherein the directly posterior direction is defined as the 12 o'clock direction) of the vertebral endplate toward the anterior-lateral region (5-6 o'clock or 6-7 o'clock point). In such cases, the dome of the intervertebral disc prosthesis may be shaped to match the corresponding recess. The surfaces of the rigid endplates that contact the adjacent vertebrae may also be provided with surface coatings or structures that promote bone in-growth after implantation.

The prosthetic endplates have attachment points or extensions for the structure connecting the disc prosthesis component to the facet joint prosthesis components. These attachment points are located at the postero-lateral edge of the endplate, generally at the 10-11 and 1-2 o'clock positions, wherein the directly posterior direction is defined as the 12 o'clock direction.

The intervertebral disc prosthesis core may be of any conventional structure that allows for relative movement of the rigid endplates with attached vertebrae that mimics or approximates the natural motion of the vertebrae in the spinal motion segment. Thus, the intervertebral prosthesis core may include mutually pivoting or sliding structures fastened to the rigid prosthesis endplates to allow angular bending and/or twisting motion about a transverse axis, an antero-posterior axis or a vertical axis. Such sliding or pivoting intervertebral prostheses are well-known. Alternatively, the disc prosthesis core may be an elastomeric material bonded to the prosthesis endplates. Such intervertebral disc prosthesis cores are well known and are disclosed, e.g., in Applicant's copending U.S. patent application Ser. No. 10/893,243, filed Jul. 19, 2004, U.S. Published Patent Application No. 2005/0043797, the entire disclosure of which is incorporated herein by reference. The intervertebral disc prosthesis core may also include polymeric transition plates between an elastomeric core and the rigid endplates, wherein the transition plates are formed from a polymer having a durometer greater than that of the elastomeric core. Such the intervertebral prosthesis cores incorporating transition plates are disclosed, e.g., in Applicant's copending U.S. patent application Ser. No. 10/779,873, filed Feb. 18, 2004, U.S. Published Patent Application No. 2005/0015150, the entire disclosure of which is incorporated herein by reference.

2.) The Facet Joint Prosthesis Element:

The facet joint prosthesis component has two operative components:

A) a prosthetic component for the superior articular process of the inferior vertebra, comprising a generally concave superior surface for interacting with a corresponding generally convex surface of a prosthesis affixed to the inferior articular process of the superior vertebra, and having a generally inferior extension or base for mounting to the inferior vertebra of the spinal motion segment, thereby supplementing or replacing the superior articular process; and B) a prosthetic component for the inferior articular process of the superior vertebra, comprising a generally convex inferior surface for interacting with the complementary generally concave superior surface of the prosthetic component for the superior articular process of the inferior vertebra.

A.) The superior articular process prosthetic component comprises two elements, an articulating element and a mounting base part. The articulating element includes an articulating surface for interacting with a corresponding articulating surface of the inferior articular prosthesis of the superior vertebra. The articulating surface of the superior articular process prosthetic component may be a generally flat surface, or may be saucer-shaped or cup-shaped. It is typically made of a rigid material of conventional use in orthopedic appliances, such as metal (e.g., stainless steel, chromium alloy, or titanium alloy), rigid polymer (e.g. high-density polyethylene or PEEK), or ceramic. The base part is an extension of the articulating part and may have various attachment mechanisms to the connecting system, to the disc prosthesis, to the transverse process, lamina and/or to the base plate.

The mounting base part of the prosthesis for the superior articular process component is made of rigid material, preferably metal, such as titanium, stainless steel or cobalt-chromium alloy, and has structure for secure fixation to the inferior vertebral body, to the connecting system to the disc prosthesis, and to the superior articular process prosthesis itself, typically to the inferior portion of the prosthesis. The mounting base part is preferably securely fixed to the vertebral bone by a specially designed oval shaped screw-expandable sleeve system, described below.

B.) The articulating part of the inferior articular process prosthetic component may have a flat surfaced, a ball-shaped, or a cone-shaped articulating structure matching the articulating part of the superior articular process prosthetic component. The radius of the articulating convex surface of the inferior articular process component is generally slightly smaller than that of the concave surface of the superior articular process component in order to provide for a proper amount of lateral rotation and bending. The inferior articular process component may be made, e.g., of metal, polymer or ceramic. The superior end or base of the inferior articular process component will typically have an inner concavity therein for accepting a trimmed tip of the inferior articular process of the superior vertebra. The inferior articular process component may further have an inwardly-directed projection extending generally from the bottom of the wall of the concavity for fixation to the inferior articular process bone. The inferior articular process of the superior vertebral body is trimmed but spared for fixation of the articulating component of the inferior articular process prosthetic component. The inferior articular process component may have other attachment points to the lamina, spinous process, and pedicle and/or to the superior rigid endplate of the disc prosthesis. The inner wall of the inferior articular process component, e.g., the inner wall of a hollow generally conical prosthesis, may have a cross-section of triangular shape to accept a complementary trimmed shape of the inferior articular process.

One embodiment of the facet joint component of the invention may comprise a conical prosthesis for the trimmed tip of the inferior articular process of the superior vertebra and a cup-shaped prosthesis for the superior articular process of the inferior vertebra. In the following, the prosthesis of the invention will be discussed generally in terms of such a cone-in-cup embodiment. However, it will be understood that the discussion is applicable to prostheses having other complementary shapes, e.g., ball joint, saucer-on-saucer, or the like, as well.

When assembled, the cone fits in the cup loosely to allow a prescribed amount of lateral bending, torsion and flexion. During extension, the tip of the cone will firmly engage the cup providing a weight bearing function and stability as in the natural facet joints. The superior articular process prosthetic component and its mounting base part or extension may be one unitary solid piece or may be assembled from two separate pieces. The interfaces between the mounting base part, the connecting structure, and cup may have variable adjustment joints, e.g. one or more universal joints, for positioning the components in a desired direction and position.

Facet joint prosthesis components that are readily adaptable to be used in the prosthesis of the invention and their operation are disclosed in Applicant's copending U.S. Published Patent Application, Publication No. 2005/0043797, the entire disclosure of which is incorporated herein by reference.

3) Inter-Connecting Structure Component:

The interconnecting system is made of rigid material, preferably metal, and provides a secure bridging connection between the rigid endplates of the disc prosthesis and the components of the facet joint prosthesis. The connecting system may be employed unilaterally, i.e., on the right or left side alone, or it may be used on both sides of the prosthesis. The connecting system may be employed between the superior endplate of the intervertebral disc prosthesis and the facet prosthesis for the superior articular process, or may be employed between the inferior endplate of the intervertebral disc prosthesis and the facet prosthesis for the inferior articular process, or both. The connecting system may be a straight or gentle "S" shaped curved rod or plate to accommodate the contour of the vertebral bone and to accommodate exiting nerve roots.

Various mechanisms for secure attachment of the connecting system to the prosthetic endplates and facet joint prosthesis are illustrated. The typical mechanisms include connecting rods with slidable engagement, and or turnbuckles for length adjustment and universal joints for adjusting direction that can be locked in position. The anterior end of such a connecting rod may have an adjustable engagement with one or both endplates of the intervertebral disc prosthesis, e.g., a slidable locking engagement in a sleeve or socket of an attachment extension or appendage from the disc prosthesis endplate. The connecting rod may have an anterior head to engage a complementary seat on the intervertebral disc prosthesis endplate, e.g., a head of hexagonal or other polygonal cross-section to match a complementary recess, or a grooved or serrated ball shaped head to fit in a complementary matching grooved or serrated socket. The posterior, or facet joint, end of the connecting rod between the inferior endplate of the intervertebral disc prosthesis and the prosthesis for the superior articular process may be provided with appropriate mechanisms for adjustment of length and for coupling to the mounting extension of the prosthesis for the superior articular process. Such mechanisms for adjusting length may include telescoping rods, sliding members, turnbuckles, or the like. The connecting rod may also incorporate one or more hinges, universal joints, or the like, for angular adjustment. The coupling mechanisms for connecting the posterior end of the connecting rod to the lower mounting extension of the facet joint prosthesis for the superior articular process may include any conventional mechanism, such as specially configured plates, screws, or the like. An embodiment of such a coupling mechanism illustrated and discussed below includes a posterior mounting head having a serrated or grooved surface that engages a corresponding serrated or grooved surface on the mounting extension of the prosthesis for the superior articular process. Such serrated or grooved surfaces, on either the connecting rod end or the mounting extension may be domed to engage a complementary concave surface on the mating part. For example, the connecting rod may have a flat surface with slidable locking engagement with the endplate of the intervertebral disc for adjustment of the length, and a dome/ball shaped grooved/serrated surface toward the mounting base extension of the facet prosthesis for the superior articular process with slidably locking and universal joint-like engagement. Once all three components (disc prosthesis endplates, connecting system and facet joints prosthesis) are assembled in the appropriate length and angle, these three components may be securely fixed each other and are securely fixed to the vertebral bone with a pedicle screw and expandable sleeve.

Surgical Procedure:

The surgical approaches for implanting the current design of disc and facet prostheses may be by combined anterior and posterior approaches; an anterior approach for the disc prosthesis and a posterior approach for the facet joint prosthesis and assembly of connecting system. However, a single posterior surgical approach is preferred. This single posterior approach dictates some specific design features of the prostheses and instruments. Surgical exposure for the access area to insert the disc prosthesis is the most important limiting factor. Most hitherto-used procedures take the route of a small exposure, often sparing the facet joint, to insert implants. This small exposure requires a small implant that can be inserted by minimally invasive surgical procedures, or a composite prosthesis that can be assembled in situ from multiple small parts during the operation. Alternatively, a prosthesis suitable for insertion through such small exposure may be a collapsible implant having a small collapsed size for insertion that is expanded after insertion. Such designs, however, have difficulty in providing adequate implant stability and biomechanical properties close to those of the natural disc. Any implant that will provide prevention of subsidence and stable biomechanics requires an adequate size of prosthetic endplates with anterior-posterior diameter in the range of 2-3 cm and mediolateral diameter in the range of 2.5-4 cm. To insert such prosthesis, it requires the access exposure areas of minimum of 2-3 cm to accommodate the narrower diameter of the prosthesis. A straight posterior approach with laminectomy will provide approximately 1-1.5 cm diameter of exposure by retracting the nerve root and dura to the midline. Any lateral approach with facet joint sparing will provide less than 1.5 cm exposure between the two exiting nerve roots. Posterior-lateral approach with resection of the superior articular process according to the invention can provide approximately 2.5-4 cm of access area of exposure that is sufficiently large enough for insertion of a disc prosthesis, guiding instruments, and retractors. A postero-lateral approach with superior articular process resection (sparing the inferior articular process) can provide a large enough exposure by retracting the nerve root and dura medially to the midline and retracting the exiting lumbar nerve (post-ganglionic) laterally. This approach spares the inferior articular process for fixation and guidance of the facet joint prosthesis.

Surgical Instruments:

The vertebral endplates can be reamed for congruous seating of a domed surface of a rigid endplate of the disc prosthesis. The surgical approach described above allows an ample room for specific reaming of the vertebral endplates by using a reamer from the posterior-lateral exposure. The reamer may be manually operated or connected to a power tool. The reamer may be generally a straight cylinder shaped or an elliptical shaped, or a flat surfaced with cutting edges on the surface. When the cylinder or elliptical reamer is used with a bilateral approach, it will produce a very unique pattern of dome in the vertebral endplate ("heart" shaped). This pattern has an intact area of bone along the posterior margin of the vertebral endplates in front of the dura that protects disc prosthesis from migrating backward. The "heart" shaped dome in the vertebral endplates can provide a very stable prosthetic fit against displacement, especially against rotation, as well as anterior and posterior extrusion.

The invention will be illustrated by the accompanying drawings which are to be considered as illustrative only and not limiting.

Certain prostheses and instruments according to the invention are illustrated and described below. The skilled practitioner will recognize that variations from the specifically-disclosed prostheses and instruments are possible without departing from the spirit and teaching of the invention, and all such variations are intended to be included with in the scope of the invention.

FIG. 1 is a lateral elevational view illustrating the normal anatomy of a spinal motion segment 110 which includes the superior vertebral body 100, the inferior vertebral body 101, the intervertebral disc 102 and the facet joints 103, with associated ligaments 106. The facet joint 103 operates between the inferior articular process 104 of the superior vertebral body 100 and the superior articular process 105 of the inferior vertebral body 101.

Figure 2A:
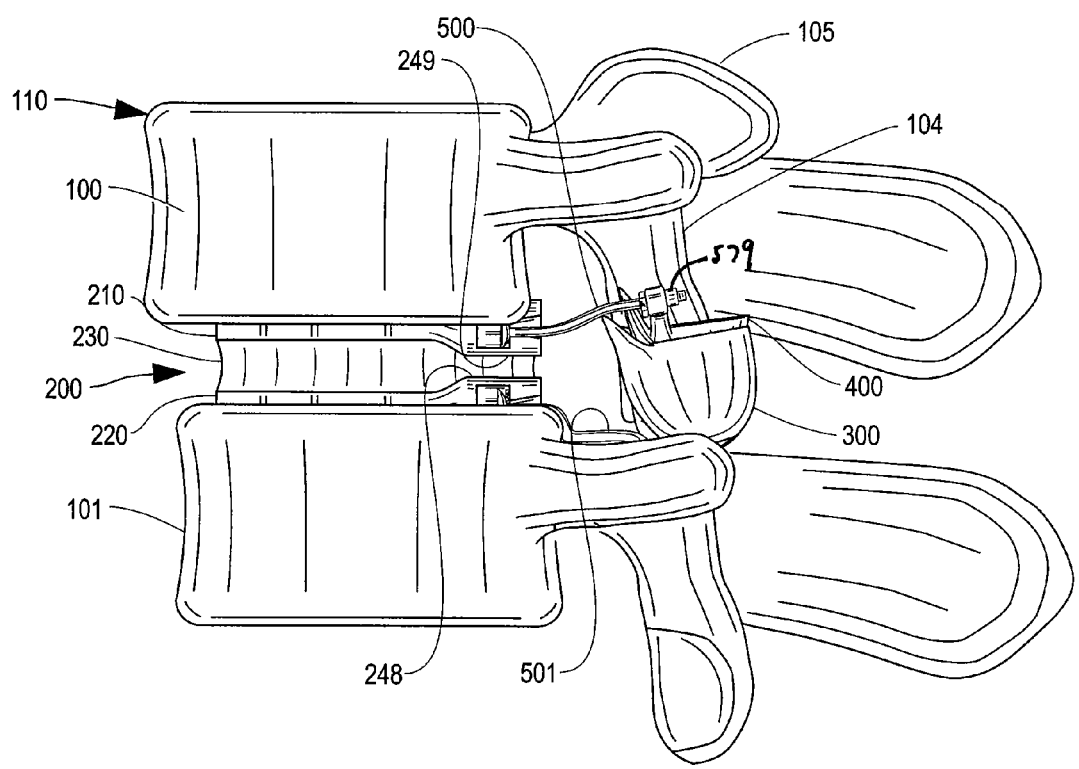
FIG. 2A shows a lateral elevational view of a human spinal motion segment having a prosthesis of the invention implanted therein.

FIG. 2A is a lateral elevational view of a spinal motion segment 110, as shown in FIG. 1, having an intervertebral disc and facet joint prosthesis of the invention implanted therein. The intervertebral disc has been at least partially replaced by the prosthesis disc component 200, including upper and lower intervertebral disc prosthesis endplates 210, 220, and core 230. At least one of the facet joints has been replaced by the facet joint prosthesis component comprising a cup element 300, replacing the superior articular process of the inferior vertebra 101, and a cone element 400, implanted on the inferior articular process 104 of the superior vertebra 100. Connecting structure in the form of connecting rods 500 and 501 has been installed to provide a generally rigid connection between the components of the disc and facet joint prosthesis. Also shown is an optional auxiliary locking nut 579 on the upper connecting rod 500. Such nuts, or equivalent clamps, or the like, can be incorporated into the prosthesis of the invention at appropriate locations if desired.

Figure 2B:
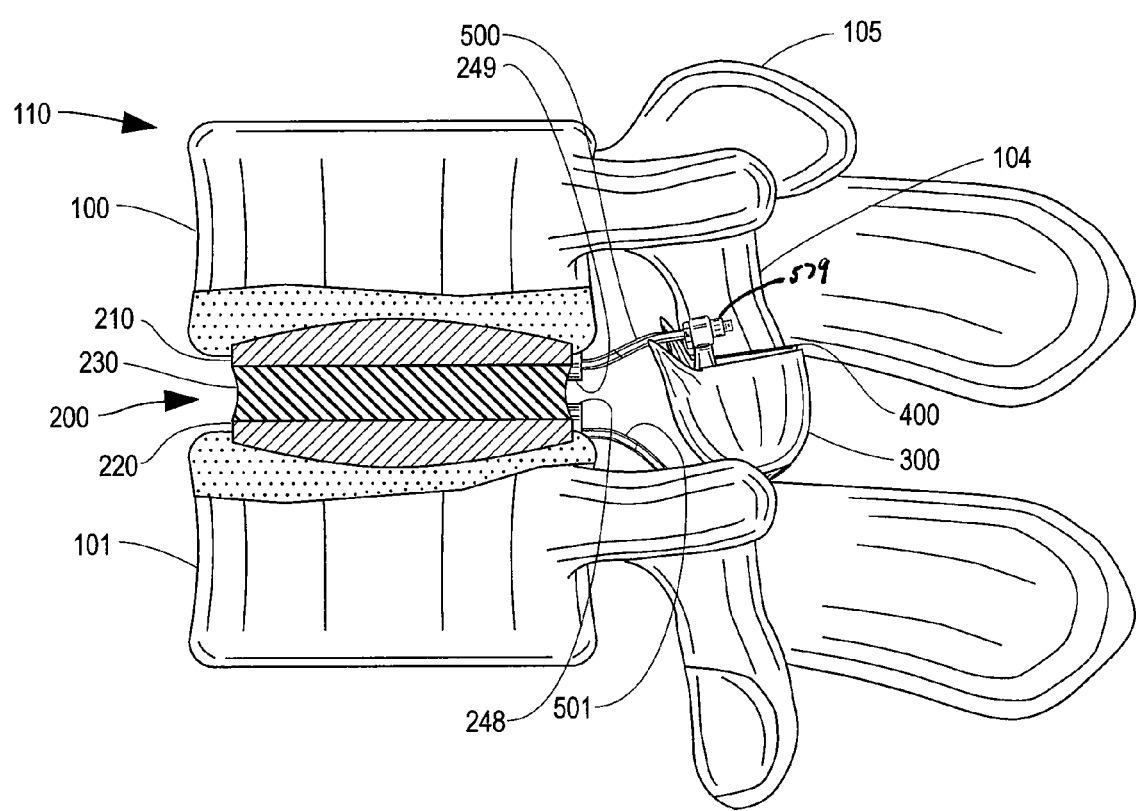
FIG. 2B shows a lateral elevational view of a human spinal motion segment having a prosthesis of the invention implanted therein, wherein the vertebrae are partially cut away to show a medial sagittal cross-section of an intervertebral disc element according to one embodiment of the invention having an elastomeric core.
Figure 2C:
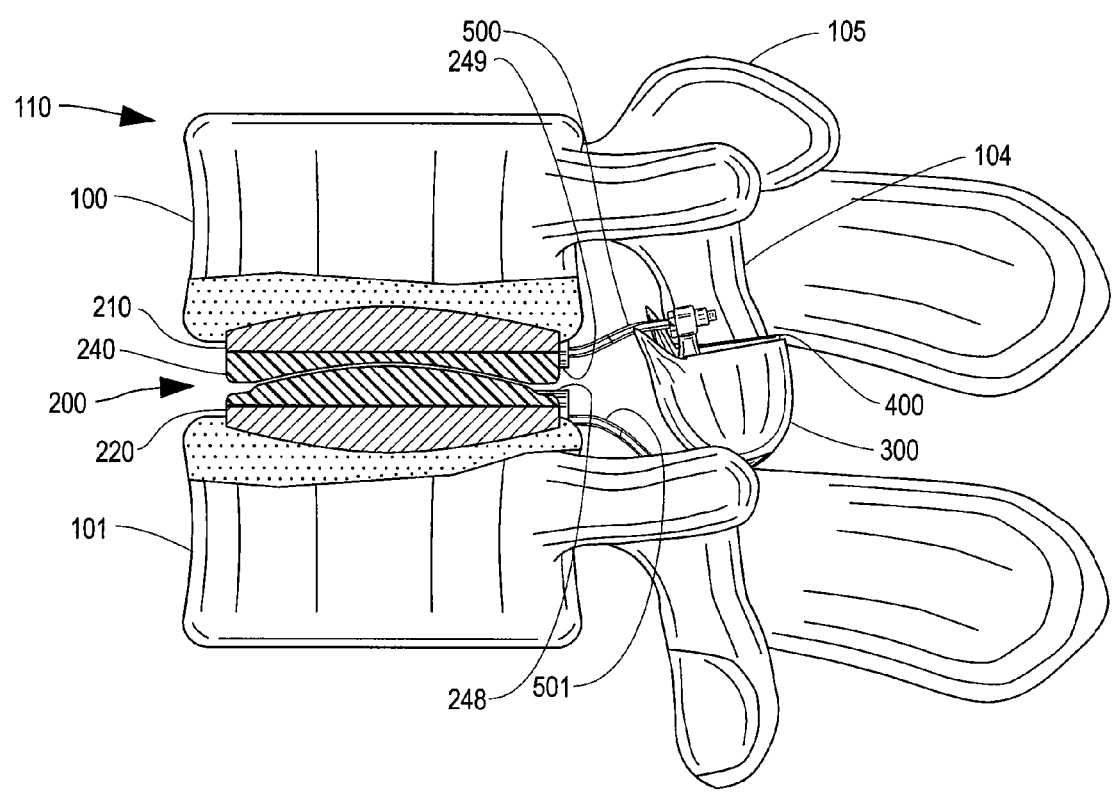
FIG. 2C shows a lateral elevational view of a human spinal motion segment having a prosthesis of the invention implanted therein, wherein the vertebrae are partially cut away to show a medial sagittal cross-section of an intervertebral disc element according to one embodiment of the invention having a sliding core.

FIGS. 2B and 2B illustrate embodiments of the invention having two alternative cores of the disc prosthesis component 200. In each figure, the upper and lower vertebrae 100, 101 of the spinal motion segment 110 have been partially cut away to show a sagittal cross-section of the core of the disc prosthesis component 200. FIG. 2B shows an embodiment having an elastomeric core 230; FIG. 2C shows an embodiment having a sliding core 240 having articulating members that allow for some relative motion between the upper and lower vertebrae 100 and 101. The disc prosthesis component 200 is preferably inserted through the posterior-lateral approach, and includes a generally dome shaped prosthetic endplate 210 for contacting the superior vertebral body 100 and a corresponding endplate 220 for contacting the inferior vertebral body 101. The disc prosthesis core 230 may be made of elastomeric polymer, as shown in FIG. 2B, or may have a sliding core such as ball-in-socket or dome-in-concavity 240, as shown in FIG. 2C. The prosthetic endplates include a connecting extension 249 for the superior prosthetic endplate 210 and a connecting extension 248 for the inferior prosthetic endplate 220 that cooperate with superior (upper) connecting rod 500 and inferior (lower) connecting rod 501, respectively. The connecting rods 500, 501 may be separate elements, as discussed in more detail below, or may simply be extensions of the prosthetic endplates.

Figure 2D:
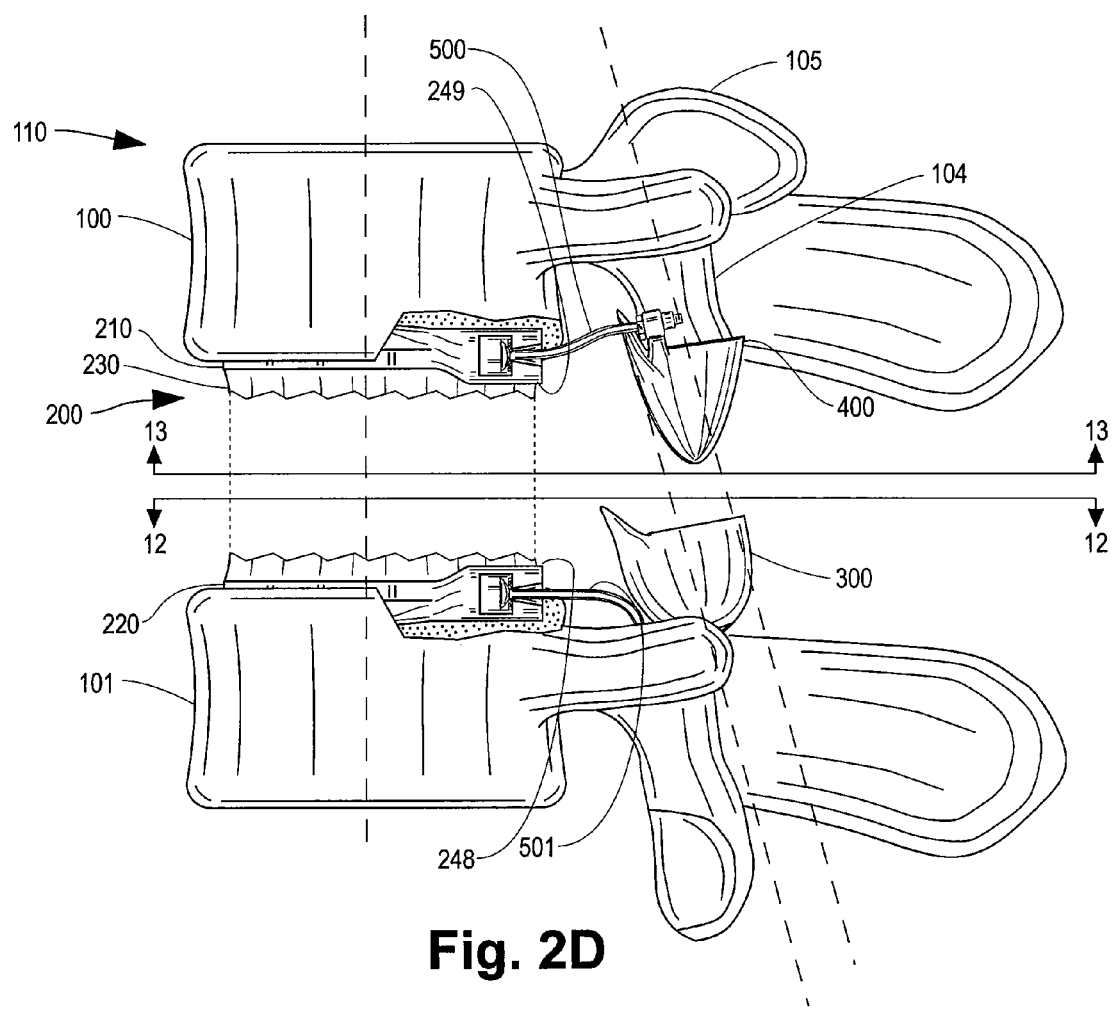
FIG. 2D is an exploded lateral elevational view of the spinal motion segment and implanted prosthesis of FIG. 2A.

FIG. 2D illustrates an exploded view of the spinal motion segment 110 with the disc and facet joint prosthesis implanted showing the angular orientation of the prosthesis components and providing a reference for certain other views of the implanted prosthesis.

FIG. 3A shows a plan view of a superior endplate 210 of the intervertebral disc prosthesis component, viewing the surface that contacts the endplate of an adjacent vertebra, a generally domed surface in this embodiment. FIG. 3B shows an elevational view in the direction indicated by the arrows 3B-3B in FIG. 3A. FIG. 3C shows a side elevational view of the prosthesis endplate 210 in the direction indicated by the arrows 3C-3C in FIG. 3A. FIGS. 3D, 3E, and 3F illustrate details of the attachment extension for the mechanical coupling apparatus as shown particularly by cross sections 3D-3D and 3E-3E, and end view 3F-3F, as indicated in FIG. 3C. The attachment extension 249 of the superior prosthetic endplate 210 includes a recess 250 having a radially grooved or serrated surface 253 and having a side channel opening 252. The inner channel has a tapered diameter 251.

Figure 3G:
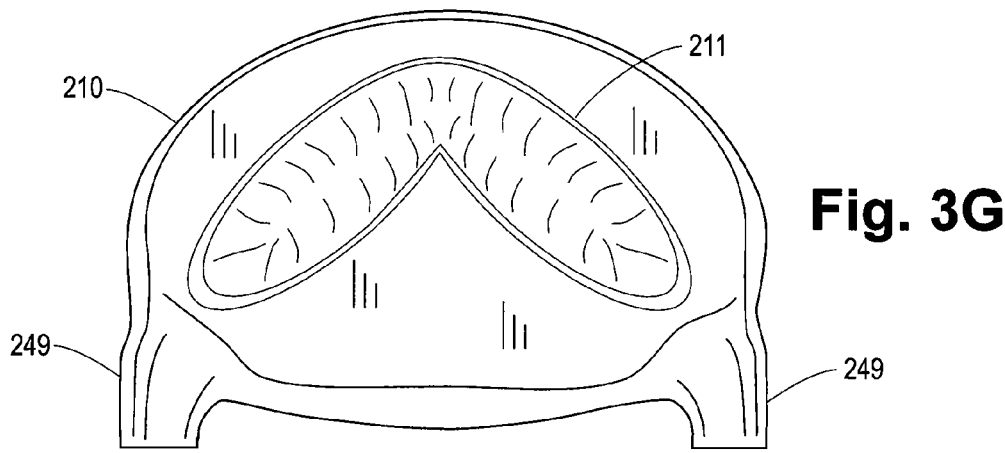
FIG. 3G is a plan view of an alternate embodiment of the endplate of FIG. 3A, wherein the vertebra-contacting surface has a "heart-shaped" raised dome or boss.
Figure 3H:
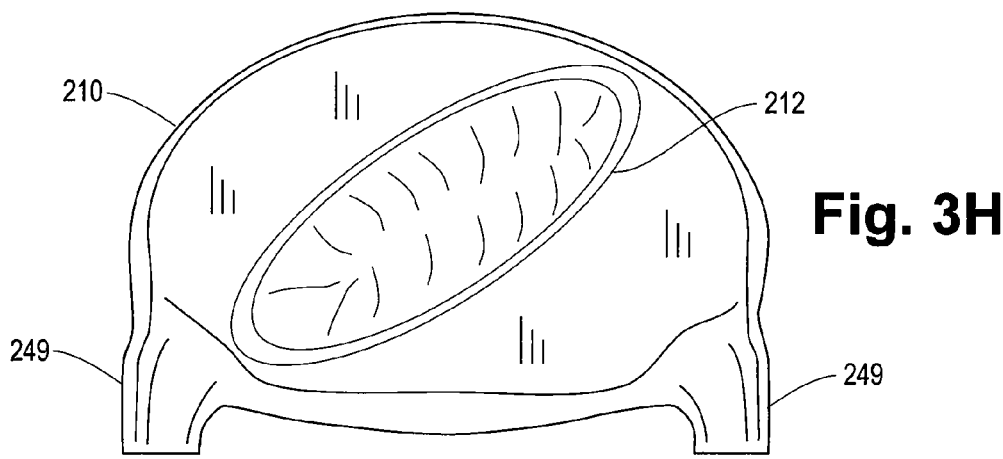
FIG. 3H is a plan view of an alternate embodiment of the endplate of FIG. 3A, wherein the vertebra-contacting surface has an oblique raised dome or boss having a generally ellipsoidal surface.
Figure 3J:
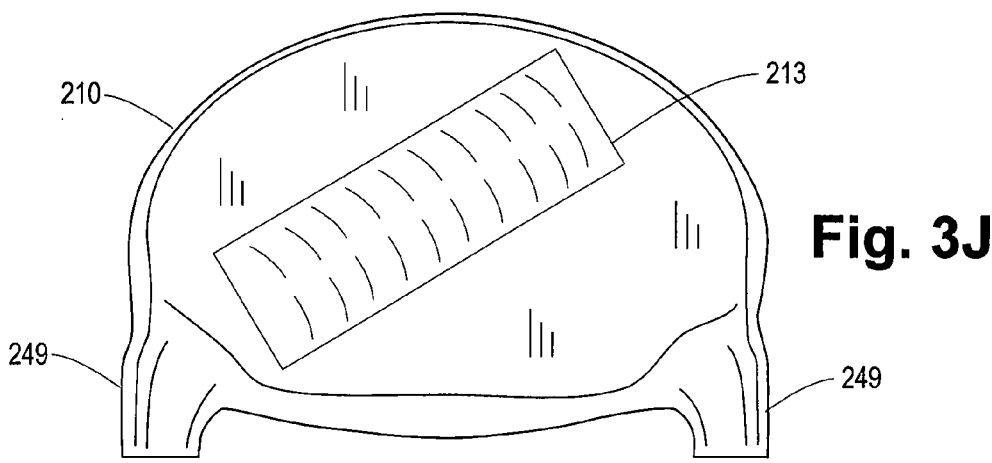
FIG. 3J is a plan view of an alternate embodiment of the endplate of FIG. 3A, wherein the vertebra-contacting surface has a raised dome or boss having a generally cylindrical surface.
Figure 17A:
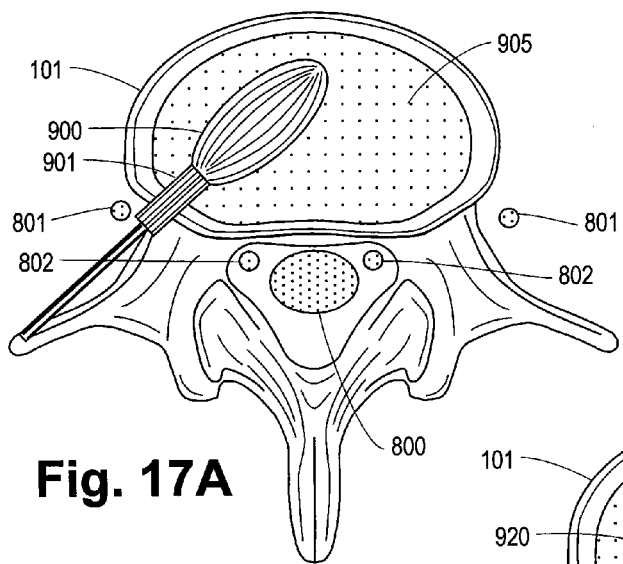
FIG. 17A is a superior view of a first step in preparing a heart-shaped depression in a vertebral endplate of an inferior vertebra of a spinal motion segment, using an appropriately shaped milling or reaming cutter.
Figure 17B:
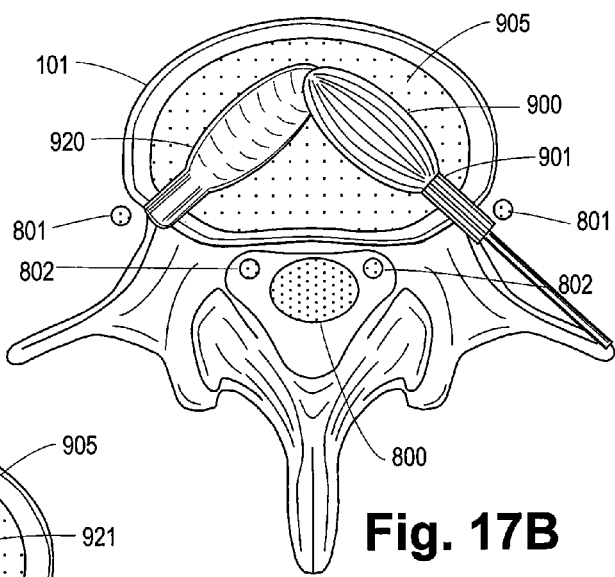
FIG. 17B is a superior view of the second step in preparing a heart-shaped depression in a vertebral endplate of an inferior vertebra of a spinal motion segment, using an appropriately shaped milling or reaming cutter.
Figure 17C:
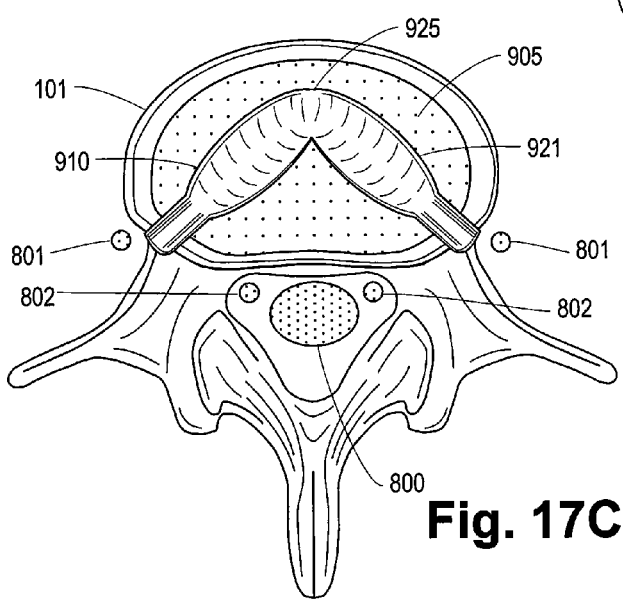
FIG. 17C is a superior view of the depressions prepared by the reaming or milling procedure illustrated in FIGS. 17A and 17B.

FIGS. 3G, 3H and 3J show specific shapes of the dome on the prosthetic endplates 210, 220 (superior and inferior) facing toward the vertebral bone. FIG. 3G has two symmetrical elliptical elevations forming a "heart" shaped elevation 211. This heart-shaped elevation is matched to a heart-shaped depression formed on the vertebral endplates by bilateral reaming with elliptical cutters, as illustrated in FIGS. 17A-C. FIG. 3H shows an embodiment having one oblique, generally elliptical elevation 212, and FIG. 3J shows an embodiment with one oblique, generally cylindrical elevation 213, each adapted to be received in a corresponding recess in a vertebral endplate made by an appropriately shaped milling cutter.

FIGS. 4A-4E illustrate the cup prosthesis 300 which substantially replaces the superior articular process 105 of the inferior vertebral body 101. FIGS. 4A-4E illustrate the cup prosthesis component for the left facet joint prosthesis; the corresponding cup component for the right facet joint will be substantially a mirror image, as will be recognized by those skilled in the art. The cup prosthesis 300 includes a cup body 312 with inner articulating surface 310, and with anterior-medial wall cut-out 311. The illustrated cup prosthesis 300 also incorporates a mounting base extension 320 having a screw hole 321. The cup element may also include a wall extension 324 that can cooperate with a similar wall extension on the cone prosthesis element 400 to protect adjacent anatomical structures and facilitate smooth movement of the facet joint prosthesis elements.

Figure 4A:
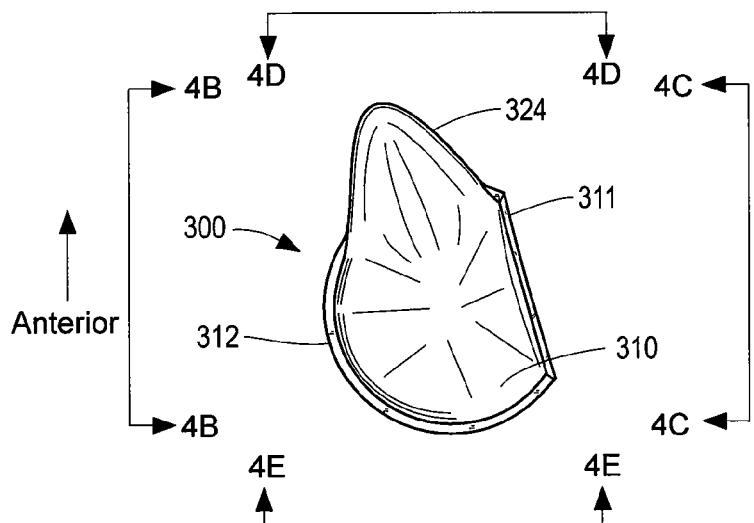
FIG. 4A is plan view of a cup component of the facet joint prosthesis element of the invention.

FIG. 4A shows a plan view and FIGS. 4B, 4C, 4D and 4E, show the lateral, medial, posterior, and anterior aspects, respectively of the cup component 400.

Figure 4B:
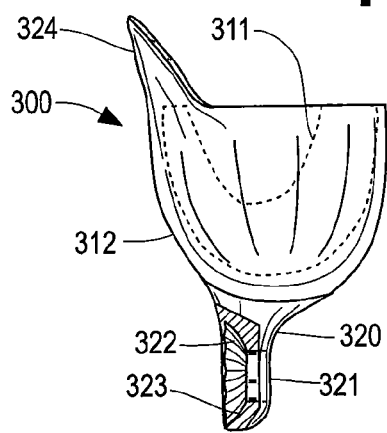
FIG. 4B is a lateral elevational view of the cup component of FIG. 4A.
Figure 4C:
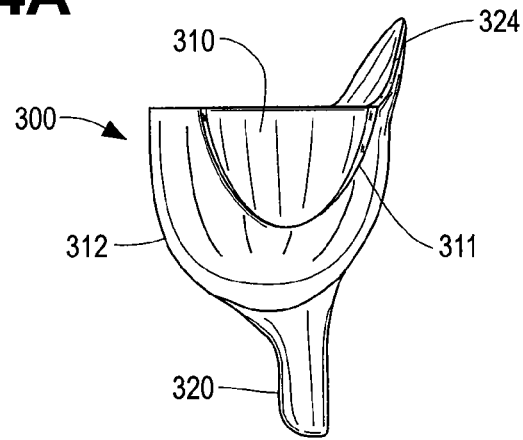
FIG. 4C is a medial elevational view of the cup component of FIG. 4A.
Figure 4D:
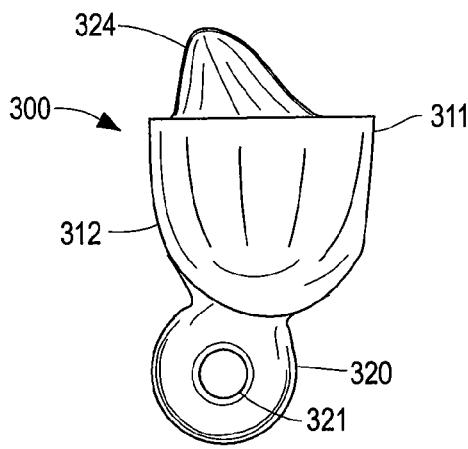
FIG. 4D is a posterior elevational view of the cup component of FIG. 4A.
Figure 4E:
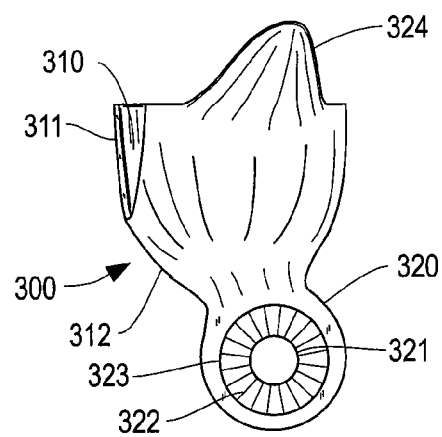
FIG. 4E is an anterior elevational view of the cup component of FIG. 4A.

FIG. 4E shows the surface of the cup base mounting extension 320 facing generally anteriorly toward the serrated connecting head 520 of the lower connecting rod 501. It has radially oriented serrations or grooves 322. The serrated surface has a concavity 323 that will match the convexity of the connecting head 520. FIG. 4B is a lateral view of the cup prosthesis 300, showing the base portion 320 in partial cross-section to show the serrated connecting concavity with grooves 322.

FIGS. 5A-5E illustrate the cone element 400 of the facet prosthesis component. As for the cup component described above, FIGS. 5A-5E illustrate the cone prosthesis component for the left facet joint prosthesis; the corresponding cup component for the right facet joint will be substantially a mirror image, as will be recognized by those skilled in the art. The cone element 400 is implanted on the inferior articular process 104 of the superior vertebral body 100. The cone-shaped prosthesis 400 has a cone-shaped outer articulating surface 410, optionally including an extension 411 of the anterior-lateral wall of the cone 400. The cone-shaped prosthesis 400 is provided with a generally triangular-shaped inner cavity 430 to be fitted onto the correspondingly trimmed inferior articular process. The internal cavity 430 preferably also has an inner projection 420 extending from the bottom of the internal cavity 430 generally along a central axis of the internal cavity 430 to fit into a hole prepared, e.g. by a conventional drilling procedure, in the bone of the inferior articular process 104. The cone element also incorporates an extension having a generally circular fixture 280, with a generally "donut" shape, for receiving the threaded end of upper connecting rod 500.

FIG. 5A shows a plan view of the cone prosthesis element 400. FIGS. 5B, 5C, 5D and 5E, show the lateral, medial, posterior, and anterior aspects, respectively of the cup component 400. FIG. 5F shows the cross-sectional area of the cone facet prosthesis 400 for the inferior articular process 104, taken along the line 5F-5F in FIG. 5A.

Figure 6A:
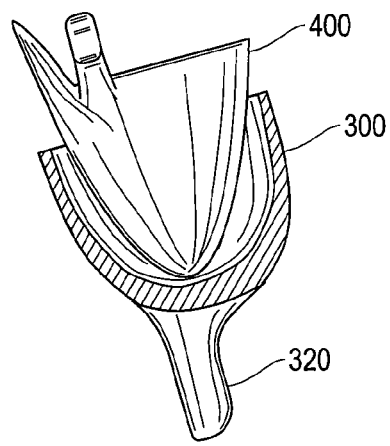
FIG. 6A is a schematic view indicating the relationship of the cup (shown in cross-section) and cone facet joint prosthesis components in one embodiment of the invention.
Figure 6B:
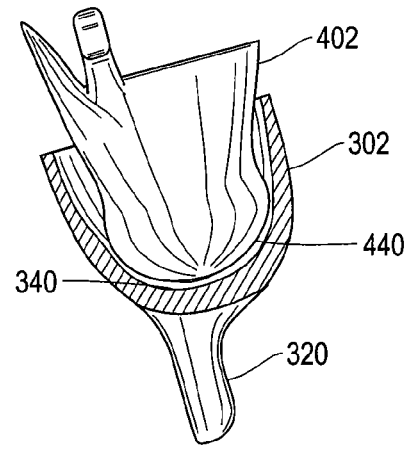
FIG. 6B is a schematic view indicating the relationship of the cup (shown in cross-section) and cone facet joint prosthesis components in an embodiment of the invention wherein the lower end of the cone element has a generally spherical or ball-shaped surface and the bottom of the internal surface of the cup element has a generally matching spherical or ball-shape.
Figure 6C:
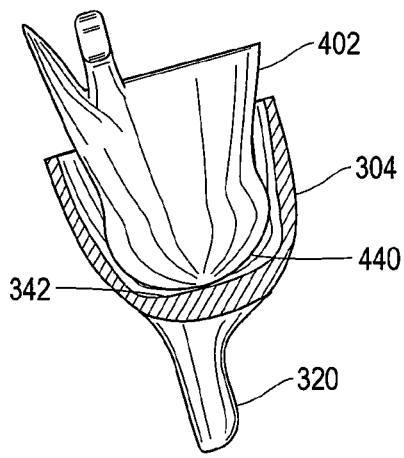
FIG. 6C is a schematic view indicating the relationship of the cup (shown in cross-section) and cone facet joint prosthesis components in an embodiment of the invention wherein the lower end of the cone element has a generally spherical or ball-shaped surface and the bottom of the internal surface of the cup element has a generally saucer-shaped configuration.
Figure 6D:
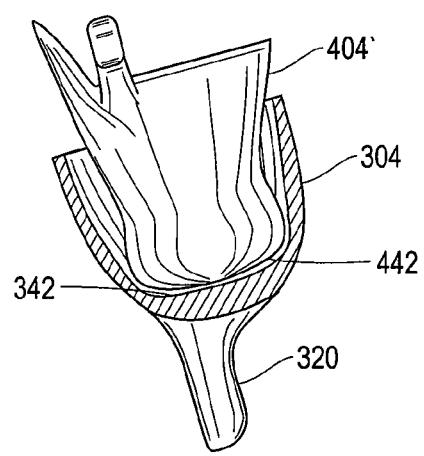
FIG. 6D is a schematic view indicating the relationship of the cup (shown in cross-section) and cone facet joint prostheses components in one embodiment of the invention, wherein the lower end of the cone element has a generally saucer-shaped or slightly curved surface and the bottom of the internal surface of the cup element has a generally saucer-shaped configuration.

FIGS. 6A-6D schematically show the relationship between various embodiments of the cone (or upper, superior) prosthesis component 400 and the cup (or lower, inferior) prosthesis component 300, of the facet joint replacement of the invention. FIG. 6A shows the relationship between the cup and cone embodiments illustrated, e.g., in FIG. 2A and FIGS. 4A-4E and FIGS. 5A-5E. The cup embodiment is shown in a generally sagittal cross-sectional view to show the interaction between the outer surface of the cone component 400 and the inner surface of the cup component 300. FIG. 6B shows the relationship between contacting surfaces of an alternate upper component 402 having a generally spherical or ball-shaped lower extremity 440, and an alternate lower component 302, having a generally spherical or ball-shaped inner surface to receive the corresponding surface of the cone element 400, thus forming a generally ball-and-socket arrangement. FIG. 6C illustrates an arrangement wherein the upper component 402 has a generally spherical or ball-shaped lower extremity 440, and an alternate lower component 304, has an internal surface with a relatively shallow curving lower portion 342 providing a saucer-shaped bottom. FIG. 6D shows an embodiment having an upper element 404 with a saucer-shaped lower extremity 442, and the cup element 304 also has a saucer-shaped bottom surface 342.

Figure 7A:
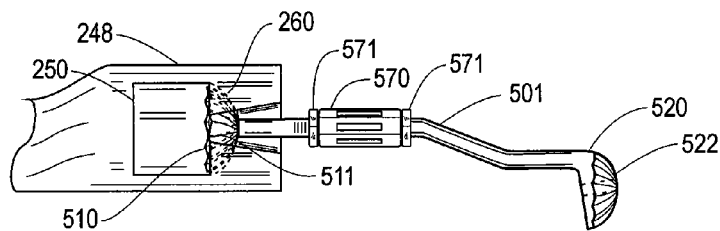
FIG. 7A shows a schematic lateral view of a lower connecting rod for the intervertebral disc and facet joint prosthesis of the invention and its interaction with the attachment extension of the lower endplate of the intervertebral disc prosthesis element, wherein the connecting rod has a serrated head and the connecting rod also incorporates an optional turnbuckle for adjusting its length.
Figure 7B:
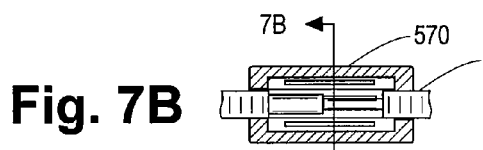
FIG. 7B shows a side elevational cross-sectional view of the turnbuckle and telescoping rod illustrated in FIG. 7A.
Figure 7C:
FIG. 7C shows a cross-sectional view of the turnbuckle illustrated in FIG. 7A and telescoping rod taken at the line indicated as 7C-7C in FIG. 7B.

The lower connecting rod 501 and its associated fastening elements, as well as certain variations of these elements, is illustrated in FIGS. 7A-7L. The lower connecting rod 501 connects a lower prosthesis endplate 220 to the cup prosthesis component 300. The connecting rod 501 need not be straight, but may have a sinuous shape or other configuration, or may be adjusted during the implantation procedure, in order to have a proper fit between the connecting extension 248 of the lower endplate 220 and the base of the cup element. The connecting rod 501 has an anterior connecting or coupling head 510 provided with serrations, grooves, or the like, indicated as 511, for engaging a corresponding serrated or grooved surface 260 of a coupling extension 248 of the lower prosthesis endplate 220. The posterior end of the rod 501 is provided with a posterior connecting head 520 also provided with serrations 522, or the like. The connecting shaft of the lower connecting rod 501 may be comprised of a plurality of sections, two telescoping sections being shown in FIG. 7A, with coupling elements therebetween, e.g., a turnbuckle 570, with associated locking nuts 571, as shown in FIG. 7A, in order to adjust the length, and/or the configuration of the connecting rod 501. FIG. 7B is a lateral elevational cross-section of the turnbuckle 570, showing the telescoping section of the lower connecting rod 501. FIG. 7C is a cross-section of the turnbuckle 570 and telescoping rod 501 taken at the line 7C-7C in FIG. 7B.

Figure 7D:
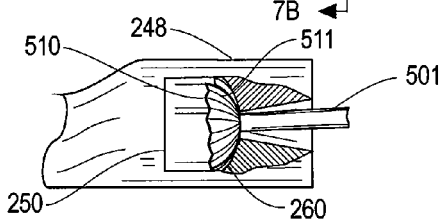
FIG. 7D illustrates schematically the angular adjustment possible in the connection between the lower connecting rod and the attachment extension of the disc prosthesis element endplate.
Figure 7E:
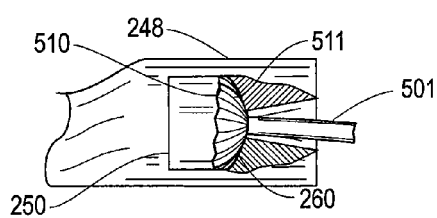
FIG. 7E shows an alternative angular relationship between the lower connecting rod and the attachment extension of the disc prosthesis element endplate.

FIGS. 7D and 7E show a detail of the connecting extension 248 of the lower endplate 220 and the anterior serrated head 510 of the lower connecting rod 501, wherein the connecting extension 248 is partially cut away to show the fit of the serrated rod head 510 with the serrated surface 260 of the connecting extension 248 at a particular angle of the lower connecting rod 501. FIG. 7D shows the connecting rod 501 fixed at one angle and FIG. 7E shows the connecting rod 501 fixed at a slightly different angle, as may be necessary or convenient in implanting the prosthesis of the invention. In either position engagement of the serrations of the rod head 510 with the serrated surface 260 of the connecting extension 248 fixes the rod 501 in a particular configuration and angle. The serrations 511 of the rod head 510 may be held in contact with the serrated surface 260 the of the connecting extension 248 by any conventional means, e.g., by posteriorly directed traction provided by the turnbuckle 570, or equivalent structure, from the posterior head 520 anchored to vertebral bone, or by insertion of a generally solid material, e.g. a hardenable or curable composition (not shown), into the recess 250 of the connecting extension 248.

Figures 7F, 7G, 7H, 7J:
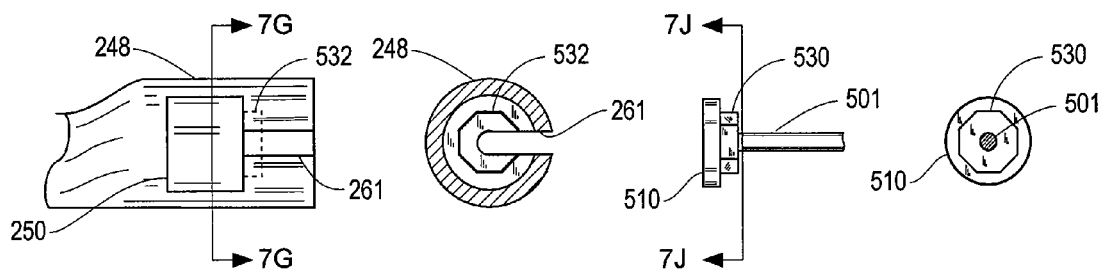
FIG. 7F shows a lateral elevational view of an alternate attachment extension of the disk prosthesis endplate element endplate, having a polygonal recess intended to receive a polygonal head of a connecting rod as illustrated in FIG. 7H
FIG. 7G shows a cross section of the attachment extension of FIG. 7F, taken along the line 7G-7G in FIG. 7F.
FIG. 7H shows a lateral elevational view of the attachment end of an alternate embodiment of a connecting rod, having a polygonal head intended to be received in a polygonal recess in an attachment extension of an endplate such as illustrated in FIGS. 7F and 7G.
FIG. 7J shows an elevational view of the rod head of FIG. 7H, taken at the line 7J-7J in FIG. 7H.
Figure 7K:
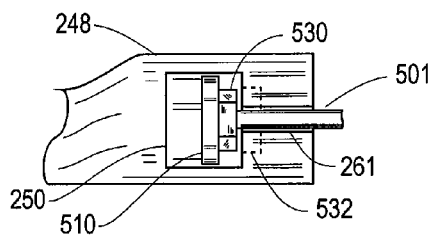
FIG. 7K illustrates a first step in the connection of a connecting rod, such as that of FIG. 7H, with an endplate attachment extension, such as that of FIG. 7F.
Figure 7L:
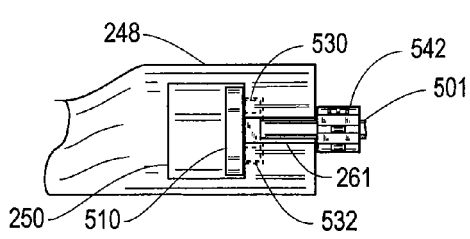
FIG. 7L illustrates the final position in the connection of a connecting rod, such as that of FIG. 7H, with an endplate attachment extension, such a that of FIG. 7F, wherein the polygonal head of the connecting rod is seated in the polygonal recess of the endplate attachment extension, and an optional securing clamp is in position.

FIGS. 7F-7L show an alternate configuration for the head 510 of the connecting rod 501 and the connecting extension 248, wherein the rod head 510 is provided with a polygonal projection or boss 530 (of octagonal cross-section, as shown, or other polygonal cross-section) that engages a corresponding polygonal recess 532 in the connecting extension 248. FIG. 7F shows a lateral elevational view of the connecting extension 248, while FIG. 7G is a cross-section taken at line 7G-7G to show the hexagonal recess therein. FIG. 7H shows the corresponding rod head 510 having a polygonal boss or projection 530 as seen in an end elevational view, taken at the line 7J-7J in FIG. 7H. FIG. 7K shows a first position in the assembly of the rod 501 to the connecting extension 248, wherein the rod head 510 has been fitted into the side opening of the connecting extension 248 with the rod 501 extending through the slotted channel 261. FIG. 7L shows the final position of the rod 501 and connecting extension 248 when the rod head 510 has bee firmly engaged with the recess. As indicated above, the rod 501 and connecting extension 248 may be retained in firm connection by any conventional means such as a clamp 542, or the like.

FIG. 8A is a somewhat enlarged schematic detail of the upper connecting system, illustrating a connecting rod 500, shown as typically having a gentle "S" shape, having at its anterior end a connecting head 550 with a grooved or serrated surface 551 similar to the connecting head 510 of the lower connecting rod 501, discussed above. The other or posterior end 560 of the connecting rod 500 is threaded, in the illustrated embodiment, and passes through the attachment ("donut") extension 280 and is provided with one or more locking nuts 290 that can be used to adjust the connection length of the rod to its proper length. A turnbuckle, as described above in connection with the lower connecting rod 501, additional clamps, locking nuts, or the like (not specifically shown), can be positioned along the rod 500 to secure exact spacing of the intervertebral disc component and the facet joint components (upper and/or lower), as is conventional in the art. FIGS.

8B-8E show the details of the attachment extension 249 and anterior connecting rod head 550 of the upper connecting structure, in parallel fashion to FIGS. 7f-7J for the lower connecting structure. FIGS. 8F-8G show the installation of the anterior rod head 550 into the connecting extension 249 of the upper disc prosthesis endplate 210, in generally parallel fashion to FIGS. 7K-7L for the lower connecting extension 248. FIGS. 8H and 8J show an alternate embodiment wherein the connecting rod 500 has a ball head 590 at its anterior end that is received in a complementary socket 291 in the connecting extension 249 and secured therein with nut 292. The method of installing and securing the anterior rod heads are generally similar for both upper and lower connecting structures, and the same detailed construction may be used in either instance.

Figure 9C:
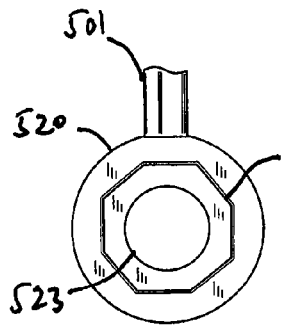
FIG. 9C is an anterior elevational view of the connecting rod posterior head of FIG. 9B.
Figure 9B:
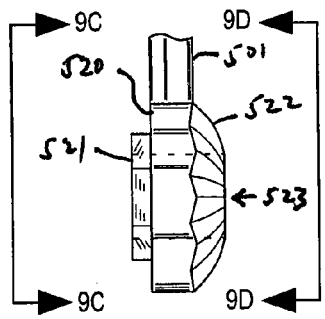
FIG. 9B is a lateral elevational view of a posterior mounting head of a lower connecting rod for mounting the cup component as shown in FIG. 9A.
Figure 9D:
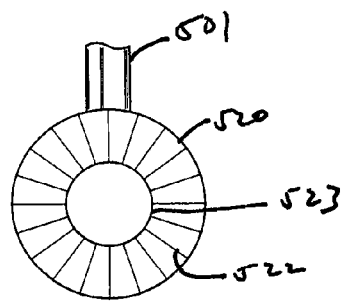
FIG. 9D is a posterior elevational view of the connecting rod posterior head of FIG. 9B.
Figure 9F:
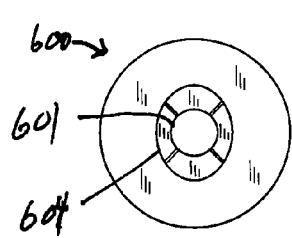
FIG. 9F is an anterior elevational view of the pedicle screw sleeve FIG. 9E.
Figure 9E:
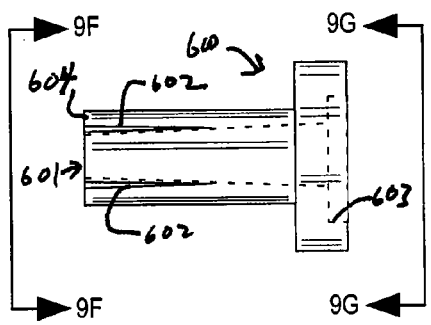
FIG. 9E is a lateral elevational view of an expandable pedicle screw sleeve for anchoring a pedicle screw in a vertebra.
Figure 9G:
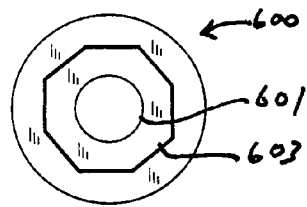
FIG. 9G is a posterior elevational view of the pedicle screw sleeve FIG. 9E.
Figure 9A:
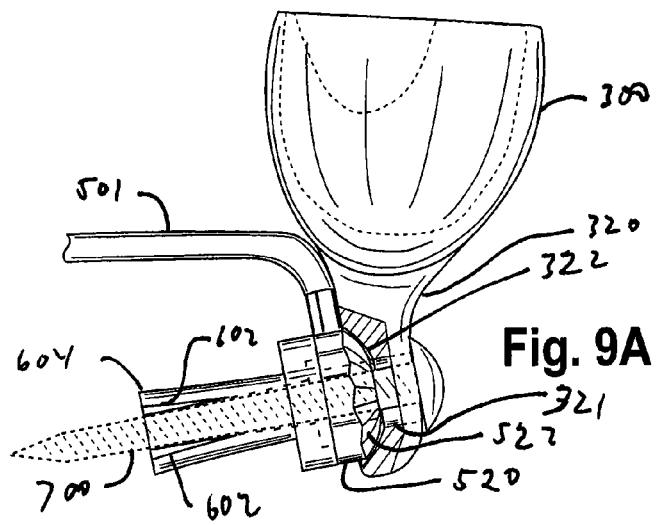
FIG. 9A is a detail elevational view in partial cross-section, of structure and components for mounting a cup component of the invention onto a lower vertebra of a spinal motion segment, as shown more fully in FIG. 20.

FIG. 9A illustrates a lateral elevational view, in partial cross-section, of an assembly of the cup prosthesis element 300, the attachment head 520 of the lower connecting rod 501, the sleeve 600 and a pedicle screw 700. The serrated or grooved surface 522 of the head 521 engages the recessed serrated or grooved surface 322 on the base 320 of the cup prosthesis 300. The polygonal boss on the generally anterior surface of the connecting head 521 engages the depression 603 of the pedicle screw sleeve 600. In an alternate embodiment, not shown, the polygonal boss may be located on the pedicle screw sleeve 600, and the complementary recess may be located on the rod head 521. In use, a generally oval hole of an appropriate size is prepared in the pedicle for receiving the expandable portion of the expandable sleeve 600. The oval recess in the pedicle generally conforms to the generally oval cross section of the pedicle. The oval end 604 of the expandable sleeve 600 is then inserted into the prepared recess in the pedicle. The polygonal boss on the attachment head 521 of the connecting rod 501 is then engaged with the polygonal recess 603 on the pedicle screw sleeve 600. Thereupon, the recessed surface 322 on the base 320 of the cup prosthesis 300 is fitted to the serrated surface cup prosthesis is fitted to the serrated or grooved surface 522 of the attachment head 521, and a pedicle screw 700 is inserted through holes 321, 523, and 601, and driven into the bone of the vertebra 101.

FIG. 9B is a lateral elevational view of the posterior attachment head 520 of the lower connecting rod 501, which engages the cup prosthesis for the superior articular process 105 of the inferior vertebra 101. FIG. 9C is an anterior elevational view of the attachment head 920, taken in the direction indicated by the arrowed line 9C-9C in FIG. 9B, and FIG. 9D is a posterior elevational view of the attachment head 920 taken in the direction indicated by the arrowed line 9D-9D in FIG. 9B The attachment head 520 is provided with a boss or projection 521 of generally polygonal cross-section (e.g., hexagonal, octagonal, or the like) on its generally anterior surface. The posterior surface of the attachment head 520 has a generally dome-shaped surface 522 that is provided with serrations, grooves, or the like, that engage the base mounting extension 320 of the cup component 300 through complementary serrations, or the like, thereon. The attachment end 520 is also provided with a hole 523 for a pedicle screw.

FIGS. 9E, 9F, and 9G illustrate an expandable sleeve 600 for use with a pedicle screw to fasten the cup prosthesis 300 to the lower vertebra 102. The expandable sleeve 600 has tapered inner screw hole 601 and slits 602 for expansion when a screw 700 is inserted. It has a polygonal, e.g., hexagonal, octagonal, or the like) depression 603 at one end to receive the matching polygonal elevation or boss 521 on the attachment head 520 of the connecting rod 501. The sleeve has an oval shaped cross-sectional area 604 for secure fixation into the normal pedicle's cross-section.

Figure 10A:
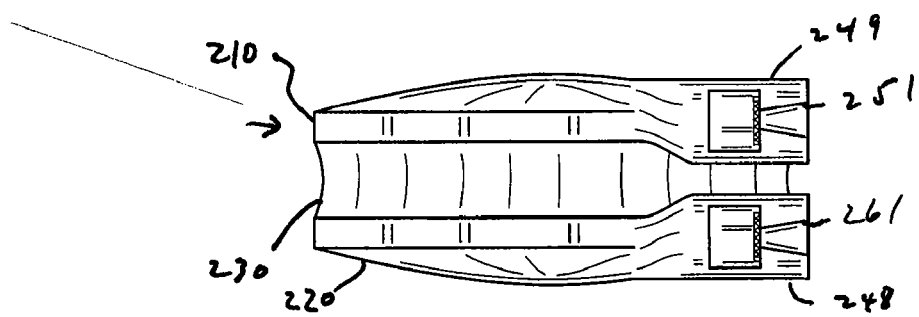
FIG. 10A shows a side elevational view of the disc prosthesis element of the disc and facet joint prosthesis of the invention.
Figure 10B:
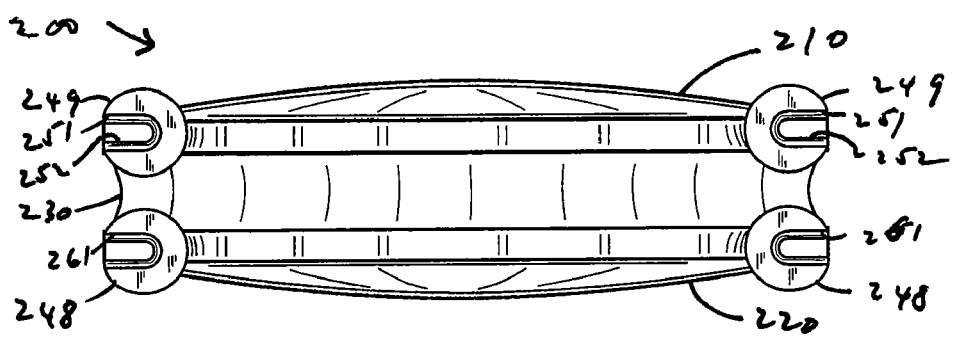
FIG. 10B shows a posterior elevational view of the disc prosthesis element of the disc and facet joint prosthesis of the invention.

FIG. 10A shows a lateral elevational view of the disc prosthesis component of the disc and facet joint prosthesis of the invention. FIG. 10B shows a posterior elevational view of the disc prosthesis component.

Figure 11:
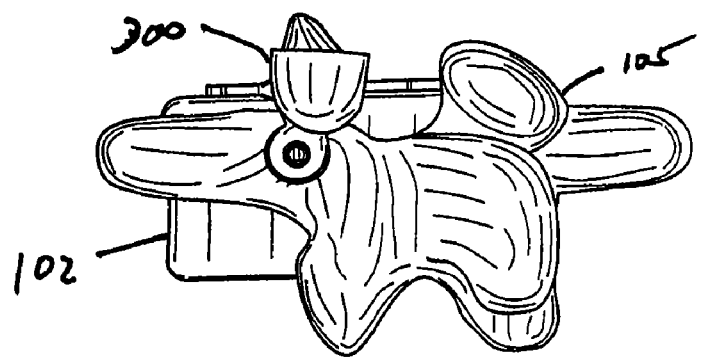
FIG. 11 is a postero-lateral view of the inferior vertebra of a spinal motion segment with a cup component in place replacing one of the superior articular processes of the vertebra.

FIG. 11 shows a posterior oblique view of the cup element 300 of the facet joint prosthesis component of the prosthesis of the invention as implanted onto the lower vertebra 101 of the spinal motion segment 110 after resection of the superior articular process 105 of the lower vertebra 101.

Figure 12:
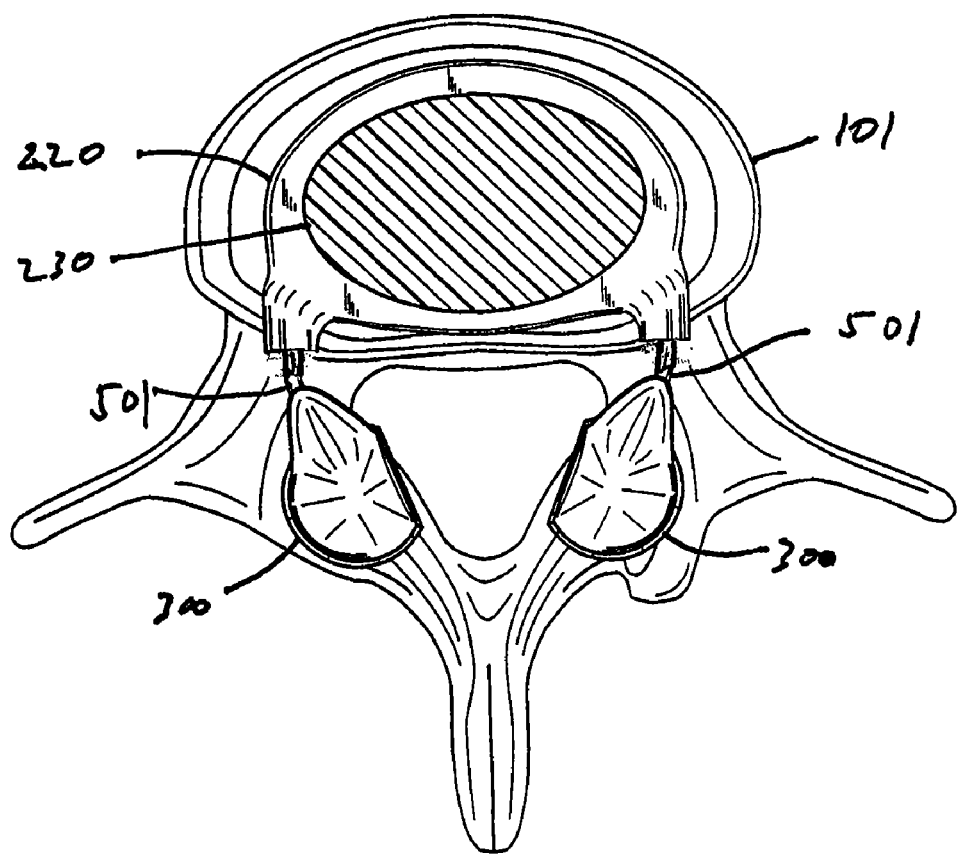
FIG. 12 is a superior plan view of the inferior vertebra of a spinal motion segment, with cup components in place, taken in the direction indicated by the line 12-12 in FIG. 2D.

FIG. 12 shows a plan view, taken in the direction indicated by the arrowed line 12-12 in FIG. 2D, showing the lower endplate 220, cup elements 300 and connecting rods 501 in their implanted positions on the lower vertebra 101 of a spinal motion segment 110.

Figure 13:
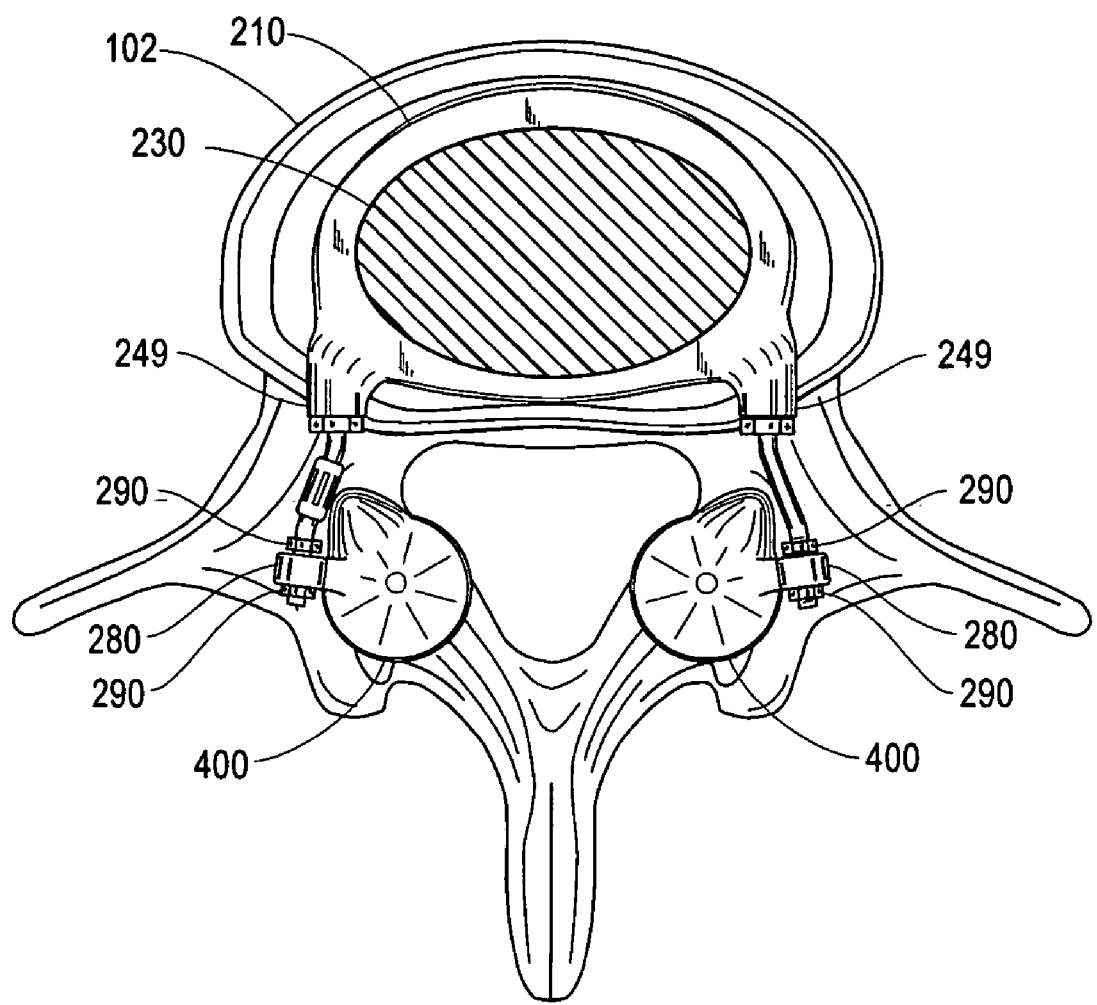
FIG. 13 is an inferior view of the superior vertebra of a spinal motion segment, with cone components in place on both inferior articular processes of the vertebra, taken in the direction indicated by the line 13-13 in FIG. 2D.

FIG. 13 shows an inferior view, taken in the direction indicated by the arrowed line 12-12 in FIG. 2D, showing the upper endplate 212, cone elements 400, and connecting rods 500 in their implanted positions on the upper vertebra 100 of a spinal motion segment 110.

Figure 14:
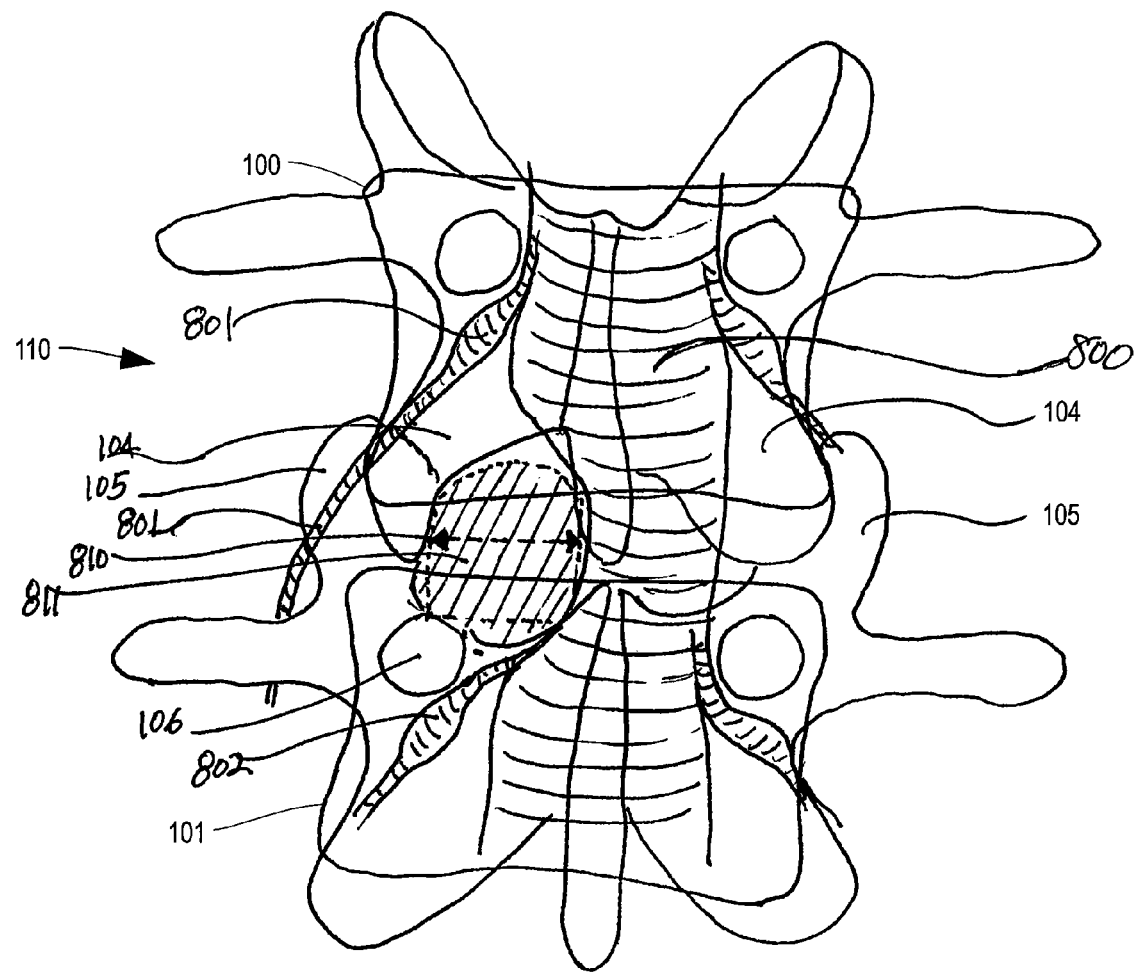
FIG. 14 is a schematic posterior elevational view of a spinal motion segment showing the surgical exposure obtainable by a posterior approach with a medial facet-sparing facetectomy of the inferior articular process of the superior vertebra.

FIG. 14 shows a posterior view of the spinal motion segment as prepared for insertion of an intervertebral disc prosthesis by a possible surgical procedure not according to the invention. In the illustrated preparation, a large laminotomy and medial facetectomy (facet sparing) have been carried out, and the dura 800 and the entering nerve root 802 have been retracted to the midline. The arrow 810 indicates the medio-lateral exposure length provided by such a procedure, providing a surgical exposure length of at most 1.7 cm for insertion of an intervertebral disc prosthesis. The general area available by this procedure is indicated by the hatched area 811.

Figure 15:
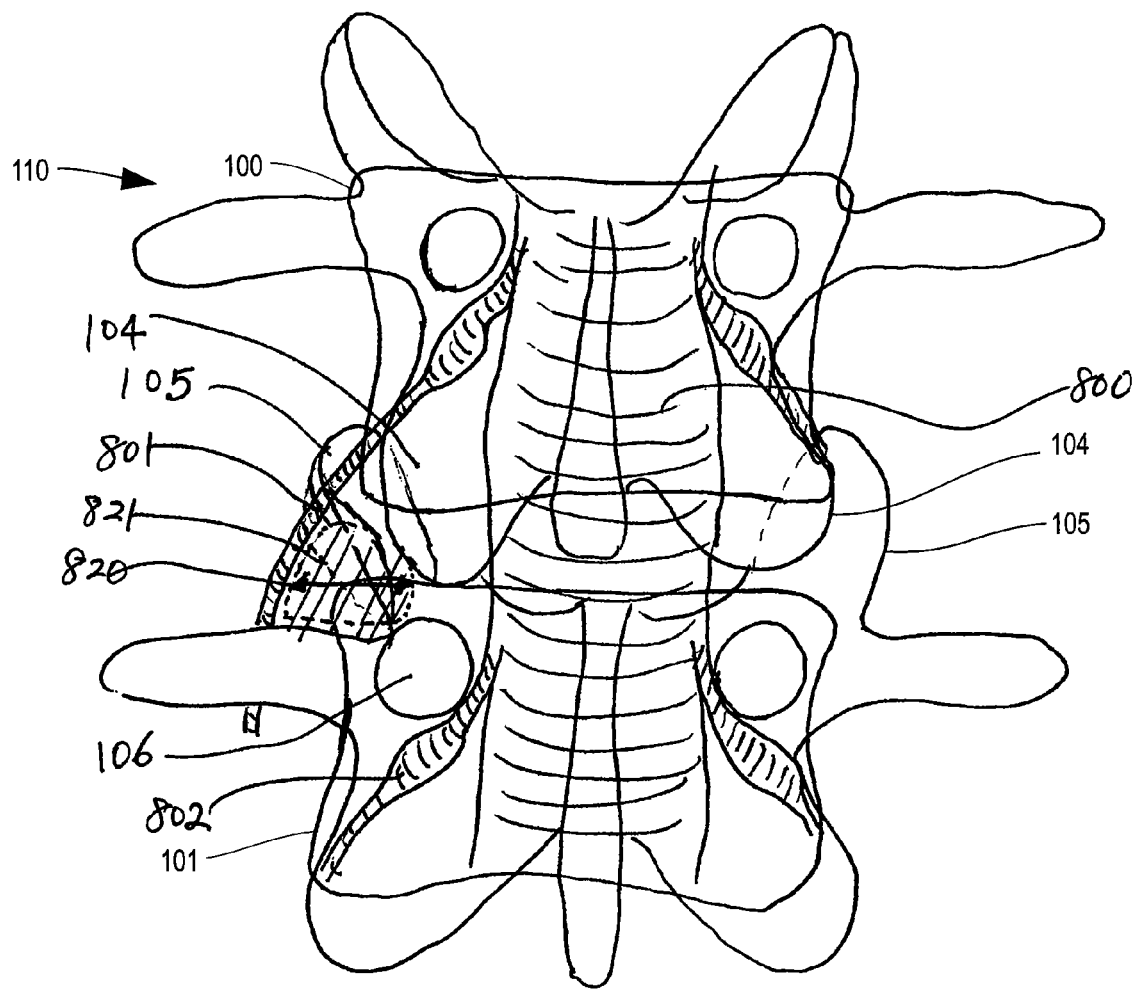
FIG. 15 is a schematic posterior elevational view of a spinal motion segment showing the surgical exposure obtainable by a postero-lateral approach with a facet-sparing partial lateral facetectomy.

FIG. 15 illustrates another possible procedure (not according to the invention) for inserting an intervertebral disc prosthesis, employing a postero-lateral approach with partial lateral facetectomy (facet sparing). In this approach, the exiting nerve root 801 and superior and inferior articular processes 104 and 105 (or residual portions thereof), limit the surgical exposure. The medio-lateral length, as shown by the double arrow 820, of exposure is small, providing only a maximum of about 1.5 cm exposure (hatched area 821).

Figure 16:
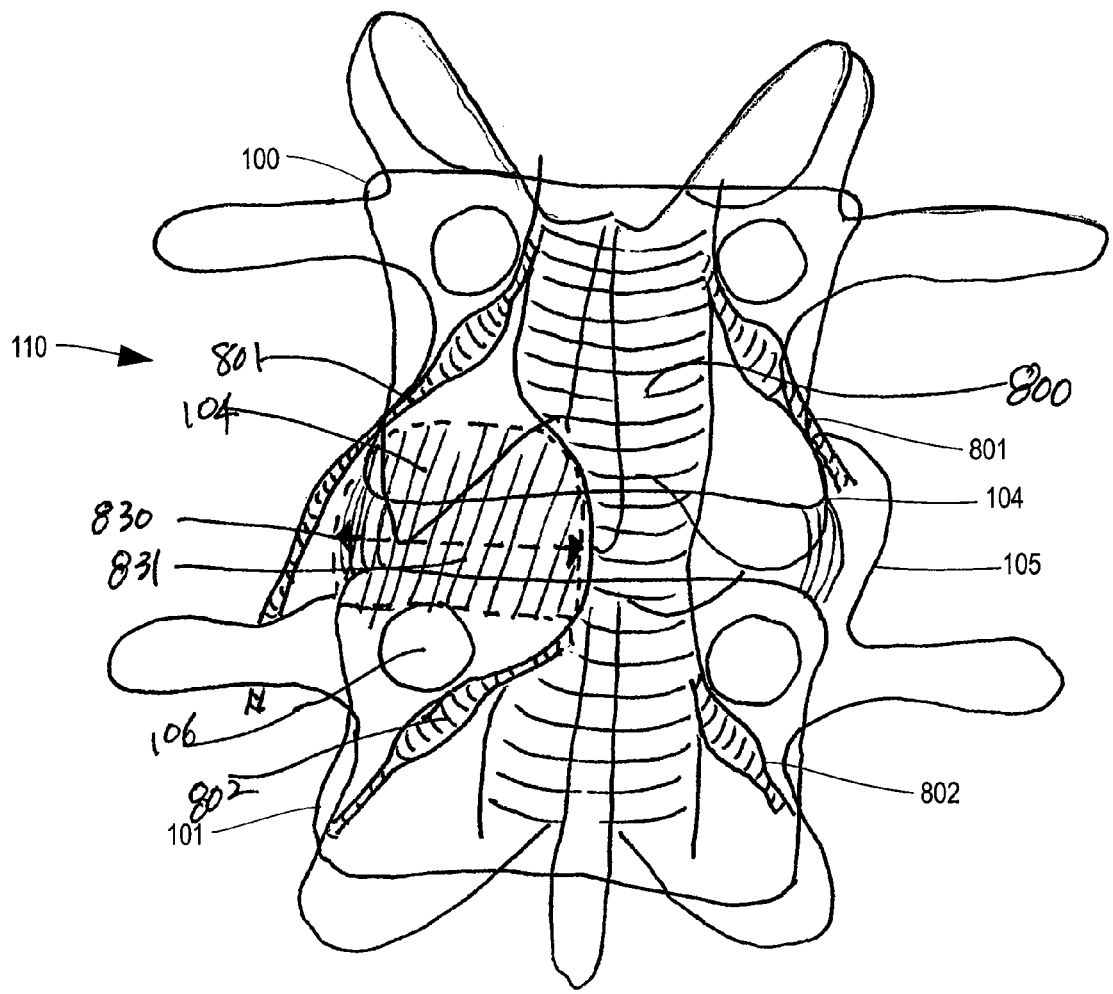
FIG. 16 is a schematic posterior view of a spinal motion segment showing the surgical exposure obtainable by a postero-lateral approach according to the invention with a superior facet resection and trimming of the inferior facet to receive the cone component of the prosthesis of the invention.

FIG. 16 shows a postero-lateral approach according to the invention with resection of the superior articular process 104 and associated facet of the inferior vertebra 102 and r trimming of the inferior articular process of the superior vertebra for implantation of the cone prosthesis 400 of the invention as a replacement for the associated facet. This procedure provides a substantially larger exposure than the two procedures described immediately above. As indicated by the double arrow 830 the width of the exposure amounts to about 2.5-5 cm. The hatched area 831 indicates the extent of the exposure above the pedicle 106 when the dura 800 and the entering nerve root 802 are retracted to the midline. Accordingly, the surgical procedure of the invention allows generally posterior insertion of disc prosthesis that has an insertion diameter greater than 1.7 cm and posterior reconstruction of one or both facet joints with a facet joint prosthesis.

FIGS. 17A-17C show the formation of a "heart-shaped" recess in a vertebra to receive a correspondingly shaped boss or projection on the endplate of an intervertebral disc prosthesis, e.g., an endplate such as illustrated in FIG. 3G. The procedure is performed with a cutter 900, of generally ellipsoidal shape, optionally equipped with a cutting collar 901, inserted into the intervertebral disc space through a postero-lateral surgical exposure. Typically, the cutter is used to perform successive milling steps from alternate postero-lateral insertions, as illustrated in FIGS. 17A and 17B, to form first 910 and second 911 generally diagonally oriented elliptically-shaped depressions in the vertebral endplate 905. The depressions so formed overlap in the anterior region of the vertebral endplate to form the "heart-shaped" recess or depression 925, as illustrated in FIG. 17C.

Figure 18A:
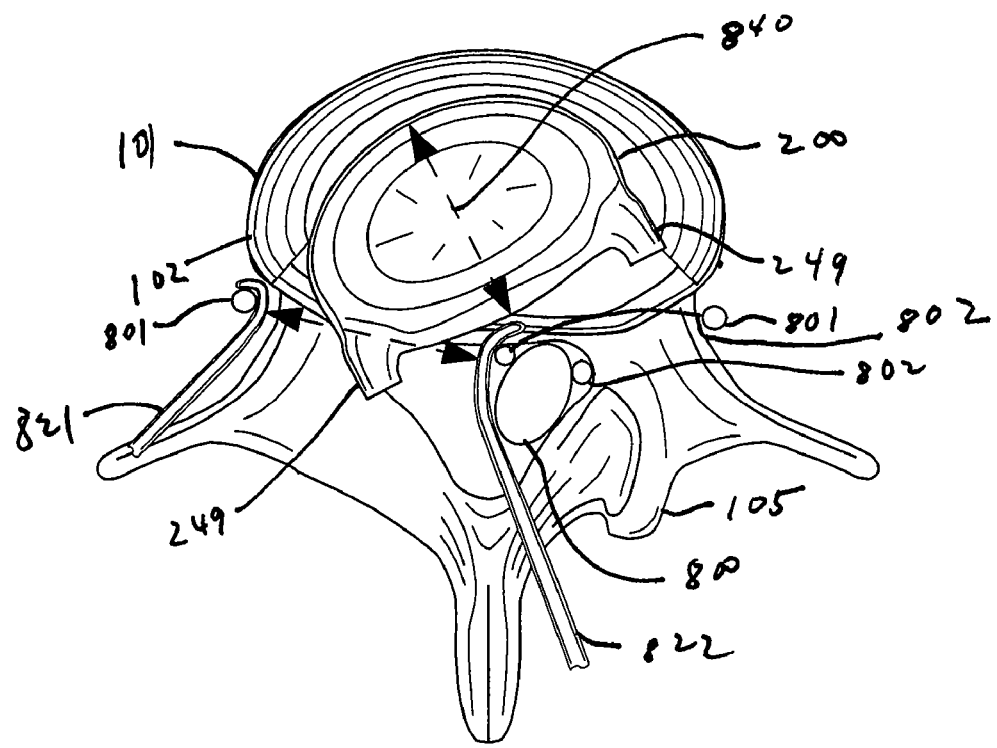
FIG. 18A is a superior view showing the insertion of the intervertebral disc element, e.g., the disc element of FIGS. 10A and 10B, through the surgical exposure prepared by the procedure of the invention.
Figure 18B:
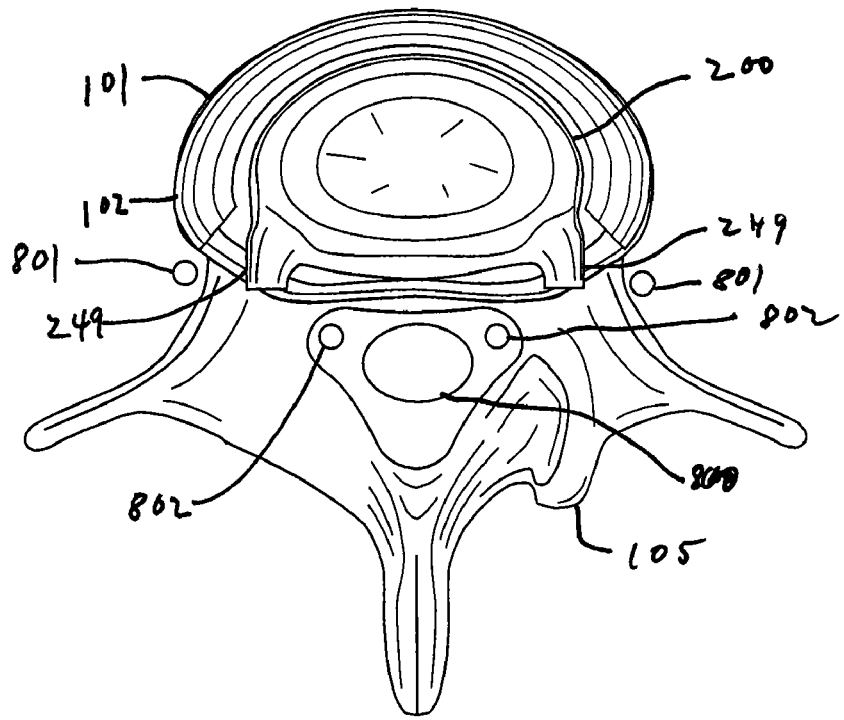
FIG. 18B is a superior view showing the inserted intervertebral disc element in position within the intervertebral space.

FIG. 18A shows insertion of a disc prosthesis through the postero-lateral surgical exposure with resection of the superior articular process as described above with associated illustrations. For clarity, the insertion procedure is viewed from a superior point of view as illustrated in FIG. 12, thus showing only the lower endplate 220 of the intervertebral disc prosthesis 200 with attachment extensions 248. This view also shows the partial resection of the annulus fibrosus 102, according to an embodiment of the invention, in which the posterior portion of the annulus fibrosus is removed to allow insertion of the prosthesis, but the anterior and lateral portions of the annulus are spared. The entering nerve root 802 with dura 800 and exiting nerve root 801 are retracted with appropriate retractors 821, 822 and adequately protected by conventional surgical procedures. When the procedure of the invention is employed, the insertion diameter of the prosthesis 840 is smaller than the surgical exposure diameter 830, allowing for insertion of a generally full-sized complete one-piece disc prosthesis through a postero-lateral surgical approach. FIG. 18B shows the intervertebral disc component 200 in position within the intervertebral space and ready for attachment of the cup and cone elements of a facet joint prosthesis component of the total prosthesis of the invention. FIGS. 18A and 18B also illustrate an embodiment of the surgical procedure of the invention, suitable for patients who have degenerative disc disease without significant facet joint pathology. In such a case, implantation of an intervertebral disc and facet joint prosthesis of the invention allows postero-lateral insertion of a substantially full-sized prefabricated intervertebral disc prosthesis, thereby avoiding the anterior approach with its accompanying major abdominal surgery, with the sacrifice of only of the facet joints (the right facet joint in the illustrated embodiment). The result of such an implantation is illustrated, e.g., in FIG. 11, which shows a postero-lateral view of the cup element implanted on a lower vertebra, and FIG. 21, which shows a posterior view of a spinal motion segment with a facet joint component (cup element and cone element) implanted therein.

Figure 19:
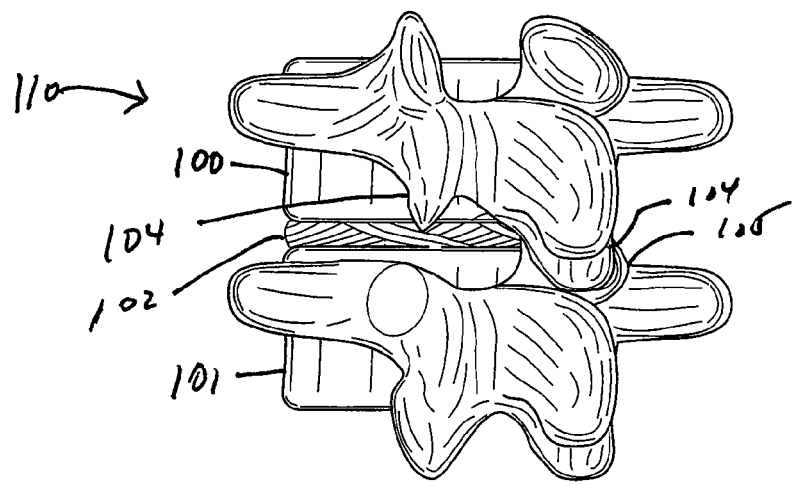
FIG. 19 is a postero-lateral view of a spinal motion segment prepared by the procedure of the invention as shown in FIG. 16.

FIG. 19 shows a postero-lateral view of the spinal motion segment after resection of the superior articular process of the inferior vertebra and trimming of the inferior articular process of the superior vertebra and retraction of the dura and nerve roots.

Figure 20:
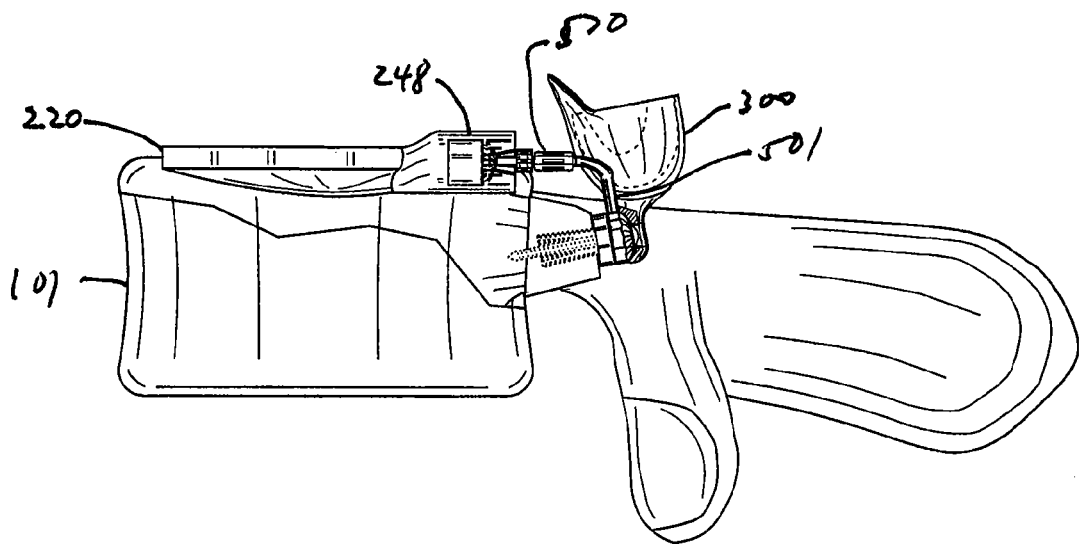
FIG. 20 is a lateral elevational view of a cup component implanted on a lower vertebra of a spinal motion segment partially cut away to show the details of the lower endplate of the disc prosthesis element and the pedicle sleeve and screw, also illustrating a turnbuckle for adjusting the length of the connecting rod.

FIG. 20 shows a lateral elevational view, partially cut away, showing the lower vertebra 101 of the spinal motion segment with the cup prosthesis 300 mounted on the resected pedicle 106 with the pedicle screw, sleeve and connected to the lower endplate 220 of the intervertebral disc prosthesis by means of the connecting rod 501.

Figure 21:
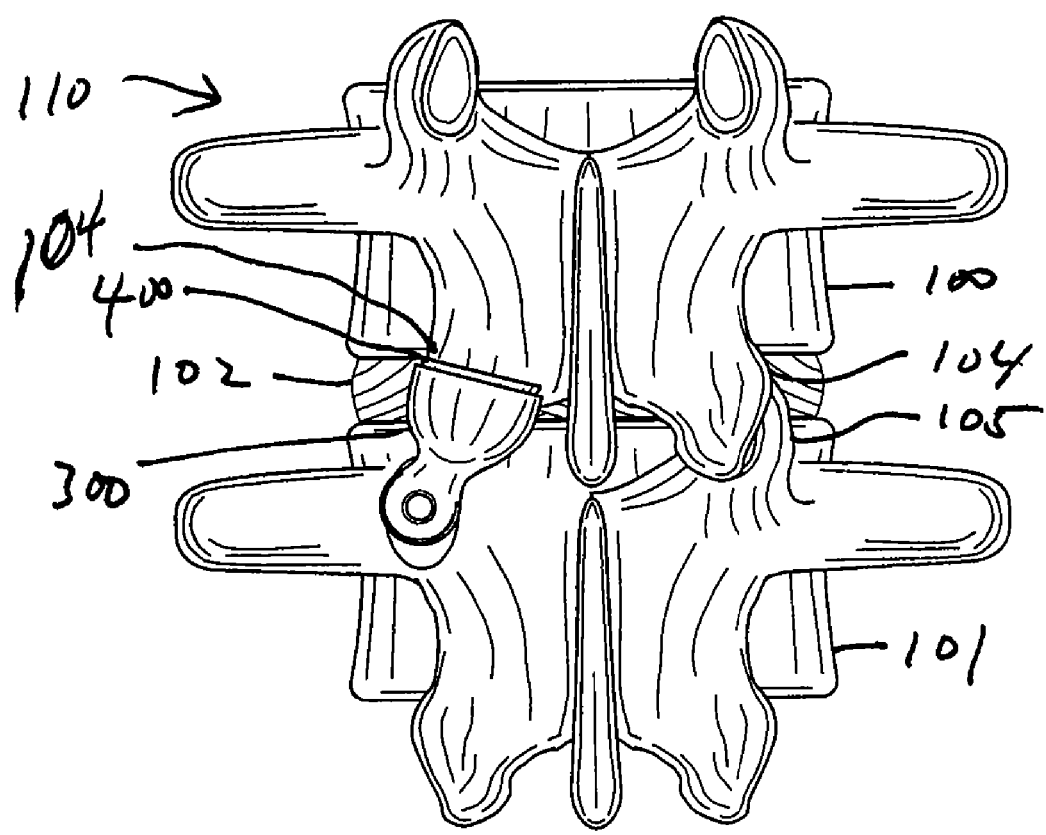
FIG. 21 is a posterior elevational view, of a spinal motion segment showing the cup and cone components implanted on one side of the segment.

FIG. 21 shows a posterior view of a spinal motion segment 100 having a disc and facet joint prosthesis of the invention implanted therein, where only one facet joint has been replaced by a facet joint prosthesis element of the invention.

Accordingly, the above-described surgical procedure of the invention provides certain advantages over the known procedures for implanting an intervertebral disc prosthesis.

Specifically, the surgical procedure of the invention including posterior surgical exposure with resection of a superior articular process and sparing of the corresponding inferior articular process provides a relatively wide surgical exposure, i.e., greater than the insertion diameter of a disc prosthesis to be implanted. Thus the procedure of the invention makes possible a generally posterior insertion of a disc prosthesis that has insertion diameter greater than 1.7 cm with posterior reconstruction of one or both facet joints by means of a facet joint prosthesis. Furthermore, it is possible to insert a disc prosthesis that has insertion diameter greater than 1.5 cm, perform a posterior reconstruction of one or both facet joints with a facet joint prosthesis, and interconnect the disc prosthesis and facet prosthesis The invention having been described above in terms of certain embodiments, it will be apparent to those skilled in that that many changes and alterations can be made without departing from the spirit or essential characteristics of the invention. All embodiments incorporating such changes or alterations are intended to be included within the invention. The present disclosure is therefore to be considered as illustrative and not restrictive, the scope if the invention being indicated by the appended claims, and all changes which come within the meaning and range of equivalency are intended to be included therein.

I claim:

1. An intervertebral disc and facet joint prosthesis, comprising:
    an intervertebral disc prosthesis element including an upper rigid disc prosthesis endplate, a lower rigid disc prosthesis endplate, and a core interposed between and attached to said rigid endplates, and
    at least one facet joint prosthesis element, each facet joint prosthesis element including an upper facet joint prosthesis component and a lower facet joint prosthesis component,
        said upper facet joint prosthesis component being constructed to cooperate with its respective lower facet joint prosthesis component, and
        at least said lower facet joint prosthesis component being rigidly fixed to the corresponding endplate by a respective rigid coupler,
        wherein said upper facet joint prosthesis component is generally conical, with a generally conical external surface and a tapered internal cavity adapted to be implanted on a tapered resected portion of an inferior articular process of a vertebra,
        said lower facet joint prosthesis component comprises a cup having an inner surface designed and configured to cooperate with said external surface of said upper facet joint prosthesis component and a base portion designed and configured for mounting on a vertebra, and
        said lower facet joint prosthesis component and said respective rigid coupler therefor are configured to be secured to each other at an adjustable angle.

2. The prosthesis of claim 1, wherein said rigid coupler comprises a rigid rod having an anterior end fastened to the corresponding endplate and a posterior end fastened to the corresponding facet joint component.

3. The prosthesis of claim 2, wherein said rigid rod comprises an anterior section and a posterior section, said sections being united by an adjustable joint.

4. The prosthesis of claim 2, wherein said adjustable joint includes a turnbuckle.

5. The prosthesis of claim 1, wherein said rigid coupler for said lower facet joint prosthesis component comprises a rigid rod having an anterior end provided with an enlarged head designed and configured to be received in a socket provided on said lower disc prosthesis endplate.

6. The prosthesis of claim 5, wherein said enlarged head and said socket are provided with complementary mating structures.

7. The prosthesis of claim 6, wherein said complementary mating structures comprise complementary serrated surfaces.

8. The prosthesis of claim 6, wherein said complementary mating structures comprise a polygonal socket on one of said lower prosthesis endplate or said enlarged head of said rigid rod and a complementary polygonal projection on the other of said lower prosthesis endplate or said enlarged head of said rigid rod.

9. The prosthesis of claim 1, wherein said rigid coupler for said lower facet joint prosthesis component comprises a rigid rod having a posterior end provided with an enlarged head designed and configured to be received in a socket provided on said lower facet joint prosthesis component.

10. The prosthesis of claim 9, wherein said enlarged head and said socket are provided with complementary mating structures.

11. The prosthesis of claim 10, wherein said complementary mating structures comprise complementary serrated surfaces.

12. The prosthesis of claim 1, wherein said upper facet joint prosthesis component is rigidly fixed to said upper endplate by a rigid coupler comprising a rigid rod extending between said upper disc prosthesis endplate and said upper facet joint prosthesis component.

13. The prosthesis of claim 12, wherein said anterior end of said rigid rod is provided with an enlarged head designed and configured to be received in a socket provided on said upper disc prosthesis endplate.

14. The prosthesis of claim 13, wherein said enlarged head and said socket are provided with complementary mating structures.

15. The prosthesis of claim 14, wherein said complementary mating structures comprise complementary serrated surfaces.

16. The prosthesis of claim 15, wherein said complementary mating structures comprise a polygonal socket on one of said disc prosthesis endplate or said enlarged head of said rigid rod and a complementary polygonal projection on the other of said prosthesis endplate or said enlarged head of said rigid rod.

17. The prosthesis of claim 12, wherein said posterior end of said rigid rod is provided with a terminal threaded portion.

18. The prosthesis of claim 1, wherein said core comprises an elastomeric member fastened to said rigid endplates.

19. The prosthesis of claim 1, wherein said upper and lower rigid endplates are provided with articulating surfaces permitting relative motion of said rigid endplates about at least one of a transverse axis and an antero-posterior axis.

20. The prosthesis of claim 1, wherein at least one of said rigid endplates has an outer surface configured to contact a vertebral endplate of an adjacent vertebra.

21. The prosthesis of claim 20, wherein said outer surface includes at least one boss.

22. The prosthesis of claim 21, wherein, in plan view, said boss has an elongated shape having a long axis oriented generally from a postero-lateral position on said endplate toward an opposite antero-lateral position on said endplate.

23. The prosthesis of claim 22, wherein said boss has a generally cylindrical profile.

24. The prosthesis of claim 22, wherein said boss has a generally ellipsoidal profile.

25. The prosthesis of claim 22, including a pair of said bosses oriented to form a single generally heart-shaped boss.

26. The prosthesis of claim 1 wherein at least one of said rigid endplates has an outer surface provided with a porous coating.

27. The prosthesis of claim 1, wherein said tapered internal cavity has a generally triangular cross-section.

28. The prosthesis of claim 1, wherein said tapered internal cavity is provided with a porous surface.

29. The prosthesis of claim 1, wherein said generally conical external surface has a radiused tip.

30. The prosthesis of claim 1, wherein a lower portion of said generally conical external surface has a generally spherical configuration.

31. The prosthesis of claim 1 wherein a lower portion of said generally conical external surface has a generally saucer-shaped configuration.

32. The prosthesis of claim 1, wherein said upper facet joint prosthesis component is rigidly fixed to said upper disc prosthesis endplate by a rigid coupler and includes a fixture to cooperate with that rigid coupler.

33. The prosthesis of claim 32, wherein said rigid coupler for said upper facet joint prosthesis component is a rigid rod extending between said upper prosthesis endplate and said upper facet joint prosthesis component, said rigid rod having a threaded posterior portion, and said fixture includes a hole for receiving said threaded posterior portion of said rigid rod.

34. The prosthesis of claim 1, wherein said inner surface of said cup incorporates a socket generally complementary to a generally spherical surface on said upper facet joint prosthesis component.

35. The prosthesis of claim 1, wherein said inner surface of said cup incorporates a generally saucer-shaped surface generally complementary to a saucer-shaped surface on said upper facet joint prosthesis component.

36. The prosthesis of claim 1, wherein said base portion of said lower facet joint prosthesis component includes a fixture to cooperate with said rigid coupler for said lower facet joint prosthesis component.

37. The prosthesis of claim 36, wherein said rigid coupler for said lower facet joint prosthesis component is a rigid rod extending between said lower prosthesis endplate and said lower facet joint prosthesis component, said rigid rod having a posterior end with an enlarged head designed and configured to be received in a socket provided on said base portion of said lower facet joint prosthesis component.

38. The prosthesis of claim 37, wherein said enlarged head and said socket are provided with complementary mating structures.

39. The prosthesis of claim 38, wherein said complementary mating structures comprise complementary serrated surfaces.

40. The prosthesis of claim 37, wherein said enlarged head is additionally provided with structure cooperating with a pedicle insert.

41. An intervertebral disc and facet joint prosthesis, comprising:
    an intervertebral disc prosthesis element including an upper rigid disc prosthesis endplate, a lower rigid disc prosthesis endplate, and a core interposed between and attached to said rigid endplates, and
    at least one facet joint prosthesis element, each facet joint prosthesis element including an upper facet joint prosthesis component and a lower facet joint prosthesis component,
        said upper facet joint component being constructed to cooperate with its respective lower facet joint prosthesis component, and
        at least one of said upper facet joint prosthesis component and said lower facet joint component being rigidly fixed to its respective one of said upper endplate and said lower endplate, wherein said lower facet joint prosthesis component comprises a body portion including a smooth, generally concave surface designed and configured to cooperate with an external surface of said upper facet joint prosthesis component and a base portion designed and configured for mounting on a vertebra, wherein said lower facet joint component is rigidly fixed to said lower disc prosthesis endplate by a rigid coupler and said base portion includes a fixture to cooperate with said rigid coupler, wherein said rigid coupler is a lower rigid rod extending between said lower prosthesis endplate and said lower facet joint prosthesis component, said rigid rod having a posterior end with an enlarged head designed and configured to be received in a socket provided on said base portion of said lower facet joint prosthesis component, wherein said enlarged head is additionally provided with structure cooperating with a pedicle insert, and wherein said structure cooperating with said pedicle insert includes a polygonal projection on said enlarged head sized and configured to cooperate with a polygonal recess in said pedicle insert.

42. An intervertebral disc and facet joint prosthesis, comprising:

an intervertebral disc prosthesis element including an upper rigid prosthesis endplate, a lower rigid prosthesis endplate, and a core connecting said rigid endplates and constructed to allow relative motion of said rigid endplates about at least one of a longitudinal axis, a transverse axis, and an antero-posterior axis, and at least one facet joint prosthesis element, each facet joint prosthesis element including an upper facet joint prosthesis component and a lower facet joint prosthesis component, said upper facet joint prosthesis component being constructed to cooperate with its respective lower facet joint prosthesis component, and said upper facet joint prosthesis component being rigidly fixed to said upper endplate by an upper rigid coupler and said lower facet joint prosthesis component being rigidly fixed to said lower endplate by a lower rigid coupler, wherein said upper facet joint prosthesis component is generally conical, with a generally conical external surface and a tapered internal cavity adapted to be implanted on a tapered resected portion of an inferior articular process of a vertebra, wherein said lower facet joint prosthesis component comprises a cup having an inner surface designed and configured to cooperate with said external surface of said upper facet joint prosthesis component and a base portion designed and configured for mounting on a vertebra, and wherein said lower facet joint prosthesis component and said lower rigid coupler are configured to be secured to each other at an adjustable angle.

* * * * *